United States Patent
Van Haute et al.

(10) Patent No.: US 6,197,542 B1
(45) Date of Patent: Mar. 6, 2001

(54) GENETIC MANIPULATIONS WITH RECOMBINANT DNA COMPRISING SEQUENCES DERIVED FROM RNA VIRUS

(75) Inventors: Eddie Van Haute, Ghent; Paul Ameloot, Bruges; Jean De Lafonteyne, Oudenaarde; Walter Fiers, Destelbergen, all of (BE)

(73) Assignee: Aveve, N.V., Merksem (BE)

( * ) Notice: Subject to any disclaimer, the term of this patent is extended or adjusted under 35 U.S.C. 154(b) by 0 days.

(21) Appl. No.: 08/901,379

(22) Filed: Jul. 28, 1997

Related U.S. Application Data

(60) Continuation of application No. 08/147,927, filed on Nov. 4, 1993, now abandoned, which is a division of application No. 07/592,206, filed on Oct. 3, 1990, now abandoned.

(30) Foreign Application Priority Data

Oct. 3, 1989 (NL) .................................... 8902452
Jul. 27, 1990 (NL) .................................... 9001711

(51) Int. Cl.[7] ........................... C12P 21/06; C12N 15/00; C12N 5/00; A01H 1/04

(52) U.S. Cl. .................. 435/69.1; 435/172.3; 435/240.4; 435/252.3; 800/205

(58) Field of Search ................................ 435/69.1, 172.3, 435/240.4, 252.3; 800/205

(56) References Cited

PUBLICATIONS

Van Emmelo et al., Virology 157 : 480–487 (1987).*
Gilboa et al., Bio Techniques 4(6) : 504–512 (1986).*
Walbot et al., Nature 334 : 196–197 (1988).*
A Dictionary of Genetics (King & Stansfield) Oxford University Press, Oxford, 1985, p. 336.*

* cited by examiner

*Primary Examiner*—Hankvel Park
(74) *Attorney, Agent, or Firm*—Hoffman & Baron, LLP

(57) ABSTRACT

The invention relates to genetic manipulations of eukaryotic organisms, with recombinant DNA comprising RNA virus derived sequences for protecting such organisms against RNA viruses or enabling inducible or tissue-specific production of foreign proteins/peptides or RNAs. One embodiment of the recombinant DNA according to the invention comprises recombinant DNA, comprising two, 12–1250 base pair long, inverted repeat nucleotide sequences with therebetween at least one nucleotide sequence which is derived from RNA virus which for its replication is dependent upon a viral RNA/RNA polymerase, said RNA virus derived sequence comprising at least cis elements for replication but no gene that codes for viral RNA/RNA polymerase and no gene that codes for viral coat protein. The invention also relates to eukaryotic or prokaryotic cells or organisms which incorporate the recombinant DNA according to the invention. Further the invention relates to a method of protecting such cells or organisms by genetically incorporating recombinant DNA according to the invention.

14 Claims, 8 Drawing Sheets

FIG. 4a

```
          10         20         30         40         50         60
           |          |          |          |          |          |
CCAAGAATACCAAATAGGTGCAAGGCCTTACTCAGCTAAAGAGTCTAAAATGGAGCTACC

GlnGluTyrGlnIleGlyAlaArgProTyrSerAlaLysGluSerLysMETGluLeuPro
                                                    ▲
          70         80         90        100        110        120
           |          |          |          |          |          |
AAACCAACACAAGCAATCAGCCGCCGAGGGTITTGTATCTTTCCTAAACTGGCTATGCAA

AsnGlnHisLysGlnSerAlaAlaGluGlyPheValSerPheLeuAsnTrpLeuCysAsn 130        140        150        160        170        180
           |          |          |          |          |          |
CCCATGGAGACGACAGCGAACAGTCAACGCTGCAGTTGTGTTCCAAAAAGATCTTCTAGC

ProTrpArgArgGlnArgThrValAsnAlaAlaValValPheGlnLysAspLeuLeuAla 190        200        210        220        230        240
           |          |          |          |          |          |
CATTGAGGATTCCGAGCATTTGGATGATATCAATGAGTGTTTCGAAGAATCTGCTGGGGC

IleGluAspSerGluHisLeuAspAspIleAsnGluCysPheGluGluSerAlaGlyAla 250        260        270        280        290        300
           |          |          |          |          |          |
ACAATCCCAGCGAACTAAGGTTGTCGCCGACGGAGCATATGCCCCCGCAAAATCCAATAG

GlnSerGlnArgThrLysValValAlaAspGlyAlaTyrAlaProAlaLysSerAsnArg 310        320        330        340        350        360
           |          |          |          |          |          |
GACCCGCCGAGTTCGTAAGCAGAAAAAGCACAAGTTTGTCAAATATCTTGTCAACGAAGC

ThrArgArgValArgLysGlnLysLysHisLysPheValLysTyrLeuValAsnGluAla 370        380        390        400        410        420
           |          |          |          |          |          |
TCGTGCCGAGTTTGGATTGCCTAAACCAACTGAGGCAAACAGACTCATGGTCCAACATTT

ArgAlaGluPheGlyLeuProLysProThrGluAlaAsnArgLeuMETValGlnHisPhe
```

FIG. 4b

```
           430       440       450       460       470       480
            |         |         |         |         |         |
CTTGCTCAGGGTGTGTAAGGATTGGGGCGTTGTTACAGCCCACGTACACGGCAACGTTGC

LeuLeuArgValCysLysAspTrpGlyValValThrAlaHisValHisGlyAspValAla 490       500       510       520       530       540
            |         |         |         |         |         |
ACTAGCTTTGCCACTGGTGTTCATTCCAACGGAAGATGATCTGCTATCACGAGCATTGAT

LeuAlaLeuProLeuValPheIleProThrGluAspASpLeuLeuSerArgAlaLeuMET 550       560       570       580       590       600
            |         |         |         |         |         |
GAACACACATGCTACTAGAGCTGCTGTACGAGGCATGGACAATGTCCAAGGCCAAGGGTG

AsnThrHisAlaThrArgAlaAlaValArgGlyMETAspAsnValGlnGlyGlnGlyTrp 610       620       630       640       650       660
            |         |         |         |         |         |
GTGGAACAATAGGTTGGGGATTGGGGGCCAGATCGGACTGGCCTTCCGGTCCAAATAGGG

TrpAsnAsnArgLeuGlyIleGlyGlyGlnIleGlyLeuAlaPheArgSerLys---Gly
                                                         ▼
           670       680       690       700       710       720
            |         |         |         |         |         |
GTGCCTTGAAAGGAGGCCAGGATTCTCCACGTCCGTTTCGCGTGGGGAACATCCTGATCT

CysLeuGluArgArgProGlyPheSerThrSerValSerArgGlyGluHisProAspLeu 730       740       750       760       770       780
            |         |         |         |         |         |
GGTGGTCATACCATCAGGGCGCCCTGAGAAACAGCGTCAGTTGTTACGCTACAGTGGTAT

ValValIleProSerGlyArgProGluLysGlnArgGlnLeuLeuArgTyrSerGlyIle 790       800       810       820       830       840
            |         |         |         |         |         |
AGGCGGCCATTTATTAATCGGCATCCACAACAACTCTCTTTCCAACTTGCGTAGGGCTT

GlyGLyHisLeuLeuIleGlyIleHisAsnAsnSerLeuSerAsnLeuArgArgGlyLeu 850       860       870       880       890       900
            |         |         |         |         |         |
GATGGAGAGAGTATTCTACGTCGAGGGGCCCAATGGGCTCCAAGACGCCCCTAAGCCCGT

METGluArgValPheTyrValGluGlyProAsnGlyLeuGlnAspAlaProLysProVal
```

FIG. 4c

```
          910       920       930       940       950       960
           |         |         |         |         |         |
CAAGGGAGCTTTCCGGACCCTTGATAAGTTTCGTGATCTCTATACTAAAAATAGTTGGCG

LysGlyAlaPheArgThrLeuAspLysPheArgAspLeuTyrThrLysAsnSerTrpArg 970       980       990      1000      1010      1020
           |         |         |         |         |         |
TCATACCCCTGTAACTAGTGAACAATTCCTAATGAATTACACGGGCAGGAAACTGACTAT

HisThrProValThrSerGluGlnPheLeuMETAsnTyrThrGlyArgLysLeuThrIle 1030      1040      1050      1060      1070      1080
           |         |         |         |         |         |
TTACAGAGAGGCGGTTGATAGTTTGTCGCATCAACCCCTTAGCTCACGAGATGCAAGCT

TyrArgGluAlaValAspSerLeuSerHisGlnProLeuSerSerArgAspAlaLysLeu 1090      1100      1110      1120      1130      1140
           |         |         |         |         |         |
AAAGACATTCGTGAAGGCCGAAAAATTAAACCTTTCTAAGAAGCCTGACCCTGCTCCCAG

LysThrPheValLysAlaGluLysLeuAsnLeuSerLysLysProAspProAlaProArg 1150      1160      1170      1180      1190      1200
           |         |         |         |         |         |
GGTCATACAACCTAGATCGCCTCGGTATAACGTTTGTTTGGGCAGGTACCTCCGACATTA

ValIleGlnProArgSerProArgTyrAsnValCysLeuGlyArgTyrLeuArgHisTyr 1210      1220      1230      1240      1250      1260
           |         |         |         |         |         |
TGAACATCACGCGTTTAAAACCATTGCCAAGTGCTTTGGGGAAATCACGGTCTTCAAAGG

GluHisHisAlaPheLysThrIleAlaLysCysPheGlyGluIleThrValPheLysGly 1270      1280      1290      1300      1310      1320
           |         |         |         |         |         |
GTTTACTCTGGAGCAACAAGGGGAAATCATGCGCTCGAAGTGGAATAAATATGTTAATCC

PheThrLeuGluGlnGlnGlyGluIleMETArgSerLysTrpAsnLysTyrValAsnPro 1330      1340      1350      1360      1370      1380
           |         |         |         |         |         |
CGTTGCGGTCGGACTTGACGCCAGTCGTTTCGACCAACACGTGTCTGTTGAAGCACTCGA

ValAlaValGlyLeuAspAlaSerArgPheAspGlnHisValSerValGluAlaLeuGlu 1390      1400      1410      1420      1430      1440
           |         |         |         |         |         |
GTATGAGCATGAATTTTATCTCAGAGATTACCCAAATGATAAACAGCTAAAATGGCTGCT

TyrGluHisGluPheTyrLeuArgAspTyrProAsnAspLysGlnLeuLysTrpLeuLeu
```

FIG. 4d

```
        1450      1460      1470      1480      1490      1500
AAAGCAGCAATTGTGCAACGTGGGAACGGCATTCGCCAGTGACGGTGTTATAAAATACAA
LysGlnGlnLeuCysAsnValGlyThrAlaPheAlaSerAspGlyValIleLysTyrLys 1510      1520      1530      1540      1550      1560
GAAGAAGGGTTGTAGAATGAGCGGAGACATGAACACGAGTTTGGGCAACTGCATTTTAAT
LysLysGlyCysArgMETSerGlyAspMETAsnThrSerLeuGlyAsnCysIleLeuMET 1570      1580      1590      1600      1610      1620
GTGCGCCATGGTCTACGGGTTGAAAGAACACTTAAACATAAATTTGTCCCTTGCAAATAA
CysAlaMETValTyrGlyLeuLysGluHisLeuAsnIleAsnLeuSerLeuAlaAsnAsn 1630      1640      1650      1660      1670      1680
TGGGGATGACTGCGTCATTGTCTGTGAGAAGCGGATTTAAAGAAATTGACGAGCAGCAT
GlyAspAspCysValIleValCysGluLysAlaAspLeuLysLysLeuThrSerSerIle 1690      1700      1710      1720      1730      1740
CGAGCCATATTTCAAGCAGTTTGGATTCAAGATGGAAGTGGAAAAACCCGTGGATACTTT
GluProTyrPheLysGlnPheGlyPheLysMETGluValGluLysProValAspIlePhe 1750      1760      1770      1780      1790      1800
TGAGCGTATAGAATTTTGCCAAACCCAGCCTGTGTTTGATGGATCCCAATATATCATGGT
GluArgIleGluPheCysGlnThrGlnProValPheAspGlySerGlnTyrIleMETVal 1810      1820      1830      1840      1850      1860
ACGCAAACCTTCAGTTGTAACATCCAAAGACGTCACCAGCCTCATCCCATGTCAAACGAA
ArgLysProSerValValThrSerLysAspValThrSerLeuIleProCysGlnThrLys 1870      1880      1890      1900      1910      1920
AGCACAATACGCAGAATGGCTGCAAGCTGTGGGTGAGTGTGGCATGAGCATCAATGGTGG
AlaGlnTyrAlaGluTrpLeuGlnAlaValGlyGluCysGlyMETSerIleAsnGlyGly
```

FIG. 4e

```
       1930      1940      1950      1960      1970      1980
GATTCCTGTTATGCAGAATTTCTACCAGATGCTCCAAACTGGCATCCGCCGCACAAAATT
IleProValMETGlnAsnPheTyrGlnMETLeuGlnThrGlyIleArgArgThrLysPhe 1990      2000      2010      2020      2030      2040
CACCAAGACCGGCGAGTTCCAGACGAACGGATTGGGGTATCACTCTAGATTTATGCATAG
ThrLysThrGlyGluPheGlnThrAsnGlyLeuGlyTyrHisSerArgPheMETHisArg 2050      2060      2070      2080      2090      2100
AGTGGCCCGGGTCCCTTCGCCTGAAACCCGTTTATCCTTCTATCTAGCTTTCGGTATCAC
ValAlaArgValProSerProGluThrArgLeuSerPheTyrLeuAlaPheGlyIleThr 2110      2120      2130      2140      2150      2160
ACCAGACCTCCAAGAAGCAATGGAGATCTTCTATGATACTCACAAGCTTGATTTGGATGA
ProAspLeuGlnGluAlaMETGluIlePheTyrAspThrHisLysLeuAspLeuAspAsp 2170      2180      2190      2200      2210      2220
TGTTATCCCGACTGATACCTACCAAGTGTCAGGAGAGCATTTGATCAATGGATTACCAAA
ValIleProThrAspThrTyrGlnValSerGlyGluHisLeuIleAsnGlyLeuProAsn

2230
CTGATGTAACGGAGGA
---CysAsnGlyGly
   ▼
```

SEQUENCE LISTING

```
(1) GENERAL INFORMATION:

(iii) NUMBER OF SEQUENCES: 13

(2) INFORMATION FOR SEQ ID NO:1:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (xi) SEQUENCE DESCRIPTION: SEQ ID NO:1:

TCCATGGGAA TTCT                                                    14

(2) INFORMATION FOR SEQ ID NO:2:

(i) SEQUENCE CHARACTERISTICS:
          (A) LENGTH: 18 base pairs
          (B) TYPE: nucleic acid
          (C) STRANDEDNESS: single
```

(D) TOPOLOGY: linear (xi) SEQUENCE DESCRIPTION: SEQ ID NO:2:

TCCATGCATG GGAATTCT                                                       18

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:3:

TCCATGCAAT CGAGGGTAGG CATGCATGGG AATTCT                                   36

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:4:

TCCATGCATG CCTACCCTCG ATTGCATGGG AATTCT                                   36

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 2..28
        (D) OTHER INFORMATION:

(xi) SEQUENCE DESCRIPTION: SEQ ID NO:5:

G CGG CCG CCC GGG TTT AGT CCT TTT AGG TT                                  30
  Arg Pro Pro Gly Phe Ser Pro Phe Arg
    1               5

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:6:

Arg Pro Pro Gly Phe Ser Pro Phe Arg
  1               5

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:7:

CATGGCTAGC AGCTGCAGGA ATTCATGCAT C                                        31

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:8:

```
CATGGATGCA TGAATTCCTG CAGCTGCTAG C                                    31
```

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:9:

```
GCTTGTGAGT ATCA                                                       14
```

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:10:

```
Asp Ser Met His Gly Asn Ser Ile
1               5
```

(2) INFORMATION FOR SEQ ID NO:11:

(i) SEQUENCE CHARACTERISTICS:
        (A) LENGTH: 2236 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 2..2236
        (D) OTHER INFORMATION:

(xi) SEQUENCE DESCRIPTION: SEQ ID NO:11:

```
C CAA GAA TAC CAA ATA GGT GCA AGG CCT TAC TCA GCT AAA GAG TCT         46
  Gln Glu Tyr Gln Ile Gly Ala Arg Pro Tyr Ser Ala Lys Glu Ser
  1               5                  10                  15

AAA ATG GAG CTA CCA AAC CAA CAC AAG CAA TCA GCC GCC GAG GGT TTT       94
Lys Met Glu Leu Pro Asn Gln His Lys Gln Ser Ala Ala Glu Gly Phe
                20                  25                  30

GTA TCT TTC CTA AAC TGG CTA TGC AAC CCA TGG AGA CGA CAG CGA ACA       142
Val Ser Phe Leu Asn Trp Leu Cys Asn Pro Trp Arg Arg Gln Arg Thr
            35                  40                  45

GTC AAC GCT GCA GTT GTG TTC CAA AAA GAT CTT CTA GCC ATT GAG GAT       190
Val Asn Ala Ala Val Val Phe Gln Lys Asp Leu Leu Ala Ile Glu Asp
        50                  55                  60

TCC GAG CAT TTG GAT GAT ATC AAT GAG TGT TTC GAA GAA TCT GCT GGG       238
Ser Glu His Leu Asp Asp Ile Asn Glu Cys Phe Glu Glu Ser Ala Gly
    65                  70                  75

GCA CAA TCC CAG CGA ACT AAG GTT GTC GCC GAC GGA GCA TAT GCC CCC       286
Ala Gln Ser Gln Arg Thr Lys Val Val Ala Asp Gly Ala Tyr Ala Pro
80                  85                  90                  95
```

```
GCA AAA TCC AAT AGG ACC CGC CGA GTT CGT AAG CAG AAA AAG CAC AAG    334
Ala Lys Ser Asn Arg Thr Arg Arg Val Arg Lys Gln Lys Lys His Lys
            100                 105                 110

TTT GTC AAA TAT CTT GTC AAC GAA GCT CGT GCC GAG TTT GGA TTG CCT    382
Phe Val Lys Tyr Leu Val Asn Glu Ala Arg Ala Glu Phe Gly Leu Pro
        115                 120                 125

AAA CCA ACT GAG GCA AAC AGA CTC ATG GTC CAA CAT TTC TTG CTC AGG    430
Lys Pro Thr Glu Ala Asn Arg Leu Met Val Gln His Phe Leu Leu Arg
            130                 135                 140

GTG TGT AAG GAT TGG GGC GTT GTT ACA GCC CAC GTA CAC GGC AAC GTT    478
Val Cys Lys Asp Trp Gly Val Val Thr Ala His Val His Gly Asn Val
        145                 150                 155

GCA CTA GCT TTG CCA CTG GTG TTC ATT CCA ACG GAA GAT GAT CTG CTA    526
Ala Leu Ala Leu Pro Leu Val Phe Ile Pro Thr Glu Asp Asp Leu Leu
160                 165                 170                 175

TCA CGA GCA TTG ATG AAC ACA CAT GCT ACT AGA GCT GCT GTA CGA GGC    574
Ser Arg Ala Leu Met Asn Thr His Ala Thr Arg Ala Ala Val Arg Gly
            180                 185                 190

ATG GAC AAT GTC CAA GGC CAA GGG TGG TGG AAC AAT AGG TTG GGG ATT    622
Met Asp Asn Val Gln Gly Gln Gly Trp Trp Asn Asn Arg Leu Gly Ile
        195                 200                 205

GGG GGC CAG ATC GGA CTG GCC TTC CGG TCC AAA TAG GGG TGC CTT GAA    670
Gly Gly Gln Ile Gly Leu Ala Phe Arg Ser Lys  .  Gly Cys Leu Glu
            210                 215                 220

AGG AGG CCA GGA TTC TCC ACG TCC GTT TCG CGT GGG GAA CAT CCT GAT    718
Arg Arg Pro Gly Phe Ser Thr Ser Val Ser Arg Gly Glu His Pro Asp
        225                 230                 235

CTG GTG GTC ATA CCA TCA GGG CGC CCT GAG AAA CAG CGT CAG TTG TTA    766
Leu Val Val Ile Pro Ser Gly Arg Pro Glu Lys Gln Arg Gln Leu Leu
240                 245                 250                 255

CGC TAC AGT GGT ATA GGC GGC CAT TTA TTA ATC GGC ATC CAC AAC AAC    814
Arg Tyr Ser Gly Ile Gly Gly His Leu Leu Ile Gly Ile His Asn Asn
            260                 265                 270

TCT CTT TCC AAC TTG CGT AGG GGC TTG ATG GAG AGA GTA TTC TAC GTC    862
Ser Leu Ser Asn Leu Arg Arg Gly Leu Met Glu Arg Val Phe Tyr Val
        275                 280                 285

GAG GGG CCC AAT GGG CTC CAA GAC GCC CCT AAG CCC GTC AAG GGA GCT    910
Glu Gly Pro Asn Gly Leu Gln Asp Ala Pro Lys Pro Val Lys Gly Ala
            290                 295                 300

TTC CGG ACC CTT GAT AAG TTT CGT GAT CTC TAT ACT AAA AAT AGT TGG    958
Phe Arg Thr Leu Asp Lys Phe Arg Asp Leu Tyr Thr Lys Asn Ser Trp
        305                 310                 315

CGT CAT ACC CCT GTA ACT AGT GAA CAA TTC CTA ATG AAT TAC ACG GGC   1006
Arg His Thr Pro Val Thr Ser Glu Gln Phe Leu Met Asn Tyr Thr Gly
320                 325                 330                 335

AGG AAA CTG ACT ATT TAC AGA GAG GCG GTT GAT AGT TTG TCG CAT CAA   1054
Arg Lys Leu Thr Ile Tyr Arg Glu Ala Val Asp Ser Leu Ser His Gln
            340                 345                 350

CCC CTT AGC TCA CGA GAT GCG AAG CTA AAG ACA TTC GTG AAG GCC GAA   1102
Pro Leu Ser Ser Arg Asp Ala Lys Leu Lys Thr Phe Val Lys Ala Glu
        355                 360                 365

AAA TTA AAC CTT TCT AAG AAG CCT GAC CCT GCT CCC AGG GTC ATA CAA   1150
Lys Leu Asn Leu Ser Lys Lys Pro Asp Pro Ala Pro Arg Val Ile Gln
            370                 375                 380

CCT AGA TCG CCT CGG TAT AAC GTT TGT TTG GGC AGG TAC CTC CGA CAT   1198
Pro Arg Ser Pro Arg Tyr Asn Val Cys Leu Gly Arg Tyr Leu Arg His
        385                 390                 395

TAT GAA CAT CAC GCG TTT AAA ACC ATT GCC AAG TGC TTT GGG GAA ATC   1246
Tyr Glu His His Ala Phe Lys Thr Ile Ala Lys Cys Phe Gly Glu Ile
400                 405                 410                 415
```

```
                                                        -continued

ACG GTC TTC AAA GGG TTT ACT CTG GAG CAA CAA GGG GAA ATC ATG CGC    1294
Thr Val Phe Lys Gly Phe Thr Leu Glu Gln Gln Gly Glu Ile Met Arg
                420                 425                 430

TCG AAG TGG AAT AAA TAT GTT AAT CCC GTT GCG GTC GGA CTT GAC GCC    1342
Ser Lys Trp Asn Lys Tyr Val Asn Pro Val Ala Val Gly Leu Asp Ala
            435                 440                 445

AGT CGT TTC GAC CAA CAC GTG TCT GTT GAA GCA CTC GAG TAT GAG CAT    1390
Ser Arg Phe Asp Gln His Val Ser Val Glu Ala Leu Glu Tyr Glu His
        450                 455                 460

GAA TTT TAT CTC AGA GAT TAC CCA AAT GAT AAA CAG CTA AAA TGG CTG    1438
Glu Phe Tyr Leu Arg Asp Tyr Pro Asn Asp Lys Gln Leu Lys Trp Leu
    465                 470                 475

CTA AAG CAG CAA TTG TGC AAC GTG GGA ACG GCA TTC GCC AGT GAC GGT    1486
Leu Lys Gln Gln Leu Cys Asn Val Gly Thr Ala Phe Ala Ser Asp Gly
480                 485                 490                 495

GTT ATA AAA TAC AAG AAG AAG GGT TGT AGA ATG AGC GGA GAC ATG AAC    1534
Val Ile Lys Tyr Lys Lys Lys Gly Cys Arg Met Ser Gly Asp Met Asn
                500                 505                 510

ACG AGT TTG GGC AAC TGC ATT TTA ATG TGC GCC ATG GTC TAC GGG TTG    1582
Thr Ser Leu Gly Asn Cys Ile Leu Met Cys Ala Met Val Tyr Gly Leu
            515                 520                 525

AAA GAA CAC TTA AAC ATC AAT TTG TCC CTT GCA AAT AAT GGG GAT GAC    1630
Lys Glu His Leu Asn Ile Asn Leu Ser Leu Ala Asn Asn Gly Asp Asp
        530                 535                 540

TGC GTC ATT GTC TGT GAG AAA GCG GAT TTA AAG AAA TTG ACG AGC AGC    1678
Cys Val Ile Val Cys Glu Lys Ala Asp Leu Lys Lys Leu Thr Ser Ser
    545                 550                 555

ATC GAG CCA TAT TTC AAG CAG TTT GGA TTC AAG ATG GAA GTG GAA AAA    1726
Ile Glu Pro Tyr Phe Lys Gln Phe Gly Phe Lys Met Glu Val Glu Lys
560                 565                 570                 575

CCC GTG GAT ATC TTT GAG CGT ATA GAA TTT TGC CAA ACC CAG CCT GTG    1774
Pro Val Asp Ile Phe Glu Arg Ile Glu Phe Cys Gln Thr Gln Pro Val
                580                 585                 590

TTT GAT GGA TCC CAA TAT ATC ATG GTA CGC AAA CCT TCA GTT GTA ACA    1822
Phe Asp Gly Ser Gln Tyr Ile Met Val Arg Lys Pro Ser Val Val Thr
            595                 600                 605

TCC AAA GAC GTC ACC AGC CTC ATC CCA TGT CAA ACG AAA GCA CAA TAC    1870
Ser Lys Asp Val Thr Ser Leu Ile Pro Cys Gln Thr Lys Ala Gln Tyr
        610                 615                 620

GCA GAA TGG CTG CAA GCT GTG GGT GAG TGT GGC ATG AGC ATC AAT GGT    1918
Ala Glu Trp Leu Gln Ala Val Gly Glu Cys Gly Met Ser Ile Asn Gly
    625                 630                 635

GGG ATT CCT GTT ATG CAG AAT TTC TAC CAG ATG CTC CAA ACT GGC ATC    1966
Gly Ile Pro Val Met Gln Asn Phe Tyr Gln Met Leu Gln Thr Gly Ile
640                 645                 650                 655

CGC CGC ACA AAA TTC ACC AAG ACC GGC GAG TTC CAG ACG AAC GGA TTG    2014
Arg Arg Thr Lys Phe Thr Lys Thr Gly Glu Phe Gln Thr Asn Gly Leu
                660                 665                 670

GGG TAT CAC TCT AGA TTT ATG CAT AGA GTG GCC CGG GTC CCT TCG CCT    2062
Gly Tyr His Ser Arg Phe Met His Arg Val Ala Arg Val Pro Ser Pro
            675                 680                 685

GAA ACC CGT TTA TCC TTC TAT CTA GCT TTC GGT ATC ACA CCA GAC CTC    2110
Glu Thr Arg Leu Ser Phe Tyr Leu Ala Phe Gly Ile Thr Pro Asp Leu
        690                 695                 700

CAA GAA GCA ATG GAG ATC TTC TAT GAT ACT CAC AAG CTT GAT TTG GAT    2158
Gln Glu Ala Met Glu Ile Phe Tyr Asp Thr His Lys Leu Asp Leu Asp
    705                 710                 715

GAT GTT ATC CCG ACT GAT ACC TAC CAA GTG TCA GGA GAG CAT TTG ATC    2206
Asp Val Ile Pro Thr Asp Thr Tyr Gln Val Ser Gly Glu His Leu Ile
```

-continued

```
                720                 725                 730                 735
AAT GGA TTA CCA AAC TGA TGT AAC GGA GGA                                                      2236
Asn Gly Leu Pro Asn  .  Cys Asn Gly Gly
                740                 745
```

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..39
        (D) OTHER INFORMATION:

(xi) SEQUENCE DESCRIPTION: SEQ ID NO:12:

```
GAT TCC ACG AGA TTT TCA GGA GCT AAG GAA GCT AAA ATG                                          39
Asp Ser Thr Arg Phe Ser Gly Ala Lys Glu Ala Lys Met
 1               5                  10
```

(2) INFORMATION FOR SEQ ID NO:13:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:13:

```
Asp Ser Thr Arg Phe Ser Gly Ala Lys Glu Ala Lys Met
 1               5                  10
```

1

GENETIC MANIPULATIONS WITH RECOMBINANT DNA COMPRISING SEQUENCES DERIVED FROM RNA VIRUS

This application is a continuation of application Ser. No. 08/147,927, filed on Nov. 4, 1993, now abandoned, which is a divisional Ser. No. 07/592,206 filed Oct. 3, 1990, abandoned.

The invention relates to the field of genetic engineering by means of DNA recombinant techniques, more particularly to the field of the genetic engineering of eukaryotic organisms, such as yeasts, fungi and particularly plants.

The invention is particularly directed to genetic manipulations which lead to resistance of the host organism against one or more RNA viruses, and to genetic manipulations which render the host organism capable of an inducible or tissue-specific production of foreign proteins/peptides or RNAs.

For such genetic manipulations recombinant DNA is used comprising one or more sequences derived from RNA virus, or, more particularly, at least one nucleotide sequence which is derived from RNA virus which for its replication is dependent on a viral RNA/RNA polymerase (i.e. an RNA-dependent RNA polymerase, which is sometimes referred to as "replicase"). These RNA viruses may belong to the group of double-stranded RNA viruses (i.e. the genome of the virus consists of double-stranded RNA), to the group of positive-strand RNA viruses (i.e. the genome of the virus consists of "sense" or messenger single-stranded RNA), or to the group of negative-strand RNA viruses (i.e. the genome of the virus consists of "antisense" single-stranded RNA).

Not all RNA viruses, however, are dependent on a viral RNA/RNA polymerase for their replication. This holds in particular for the viruses belonging to the family of Retroviridae, which for their multiplication are dependent on DNA replication after the genomic RNA is transcribed into DNA by means of reverse transcriptase.

Examples of RNA viruses which for their replication are dependent on a viral RNA/RNA polymerase, are double-stranded viruses from the families of Reoviridae and Birnaviridae, negative-strand viruses from the families of Arenaviridae, Bunyaviridae, Orthomyxoviridae, Paramyxoviridae and Rhabdoviridae, and positive-strand viruses from the families of Togaviridae, Flaviviridae, Coronaviridae, Nodaviridae, Picornaviridae and Caliciviridae. Concrete examples of positive-strand viruses with a plant host are Tobacco Mosaic Virus, Tobacco Necrosis Virus, Brome Mosaic Virus, Cucumber Mosaic Virus, Tobacco Streak Virus, Tobacco Rattle Virus, Cowpea Mosaic Virus, Tomato Black Ring Virus, Potato Y Virus, Turnip Yellow Mosaic Virus, Tomato Bushy Stunt Virus, Southern Bean Mosaic Virus, Barley Yellow Dwarf Virus, Potatovirus X, Sugar Beet Yellows Virus, Carnation Latent Virus, Carnation Ringspot Virus, Barley Stripe Mosaic Virus, Alfalfa Mosaic Virus, Pea Enation Mosaic Virus and Tomato Spotted Wilt Virus.

Subject to the above-mentioned limitation to RNA viruses which for their replication are dependent on a viral RNA/RNA polymerase, the term "RNA virus" as used herein includes viruses and virusoids which for their replication are dependent on the help of another (helper) virus. As is well known, RNA virus infections may be accompanied by coinfections of, for instance, satellite viruses with a coat protein of their own, satellite RNA which is packed in mixed particles, and virusoids (a small circular RNA genome, packed in mixed particles). The term "RNA virus" as used herein also includes viroids, i.e. autonomous small bare RNA molecules. The further explanation of the invention in the experimental section to follow will be given with reference to an RNA satellite virus, viz. the Satellite Tobacco Necrosis Virus (STNV), a small plant virus ($1.85 \times 10^3$ kD), which for its replication is entirely dependent on the presence of the helper Tobacco Necrosis Virus (TNV). The RNA genome of STNV contains 1239 nucleotides and codes for a coat protein of 195 amino acids.

The invention comprises incorporating genetic information into the genome of eukaryotes by means of genetic engineering, which information does not as such, nor through transcription products derived therefrom, constitute a burden to the host, and yet accomplishes a very effective protection of the host against viral infections, or enables an inducible or tissue-specific, very efficient production of foreign proteins (or peptides) or RNAs. The genetic information to be incorporated according to the invention comprises an expression-cassette for the host to be transformed containing two, 12–250 base pair long, inverted repeat nucleotide sequences with therebetween at least one nucleotide sequence which is derived from RNA virus which for its replication is dependent on a viral RNA/RNA polymerase, said RNA virus derived sequence comprising at least cis elements for replication, but no gene that codes for viral RNA/RNA polymerase and no gene that codes for viral coat protein.

The genome of RNA viruses which for their replication are dependent on a viral RNA/RNA polymerase comprises various cis elements, i.e. elements or functions which function only for the nucleic acid by which they are encoded, such as structure elements of the nucleic acid. In addition to cis elements for replication (including in any case the binding site for an RNA/RNA polymerase) the genome of RNA viruses mostly also includes cis elements for transport (the binding site of transport proteins), cis elements for packing the nucleic acid in phage envelopes to form virus particles, and cis elements for translation of messenger RNA into protein, in particular coat protein. Examples of trans elements of the genome of RNA viruses are the genes which code for coat protein, transport protein and RNA/RNA polymerase.

An essential element of the invention is that the expression cassette incorporated into the genome of the host leads to transcription of the sequence derived from RNA virus to form a messenger RNA molecule with a panhandle structure. No strict requirements are set to the elements of the expression cassette which regulate this transcription, such as in particular the transcription promoter. The promoter may be, and in many cases will even preferably be, a relatively weak promoter so that the host will be virtually unburdened by this transcription and the transcription products formed in the process. Suitable promoters are known for many organisms. Naturally the expression cassette should also comprise a suitable polyadenylation site, while the expression cassette is flanked at both ends by so-called integration sites enabling integration into the genome of the intended host.

Various experiments have demonstrated that a successful expression in the host of the viral genetic information incorporated into the genome requires the presence of two, 12–250 base pair long, inverted repeat nucleotide sequences flanking the DNA in-between. These inverted repeat nucleotide sequences may for instance consist of dG-dC base pairs or dC-dG base pairs. The fact that the presence of inverted repeat nucleotide sequences leads to both replication and expression in infected cells of the host, is ascribed to the formation of RNA molecules with a stabilizing panhandle structure (see Van Emmelo et al., Virology 157, 1987, 480–487). For this purpose it is necessary that the inverted repeat nucleotide sequences have a length of at least 12 base pairs. Preferably, however, the inverted repeat nucleotide sequences have a length of at least 15 base pairs. Inverted repeat nucleotide sequences of a length of more than 250 base pairs are not very practical. Preferably, they are not longer than about 50 base pairs.

A further essential feature is the absence of RNA/RNA polymerase (or replicase), or the gene coding therefor, so that the amount of RNA virus-specific messenger RNA present in the cells of the host due to transcription is not further increased. When the RNA virus derived sequence to be incorporated is derived from a satellite virus, such as STNV, this requirement is automatically satisfied because the STNV genome does not contain an RNA/RNA polymerase gene (which explains why the satellite virus depends for its replication on the helper virus, which provides the required RNA/RNA polymerase).

According to the invention it is further of great importance that no viral coat protein is produced and that the nucleotide sequence derived from RNA virus does not contain a gene that codes for viral coat protein.

Finally it is also essential according to the invention that the messenger RNA derived from RNA virus contains at least those elements which in the presence of RNA/RNA polymerase enable replication. In other words, at least cis elements for replication should be present. Depending on the object contemplated, it may be desirable that other elements of the viral genome are present as well. Thus, in particular in the case of protection of the host against virus infections, it is preferable that the genetic information incorporated into the genome of the host also comprises cis elements for transport.

On the other hand, it is not necessary, according to the invention, that the sequence derived from RNA virus is incorporated into the genome in the sense orientation. The same holds for the orientation of other sequences located between the inverted repeat nucleotide sequences, such as a sequence coding for a ribozyme and a sequence coding for a type-foreign protein/peptide. Owing to the fact that according to the invention both a sense orientation and an antisense orientation can be chosen, it is possible to accomplish both a maximum protection under normal, infection-free conditions and an adequate reaction in the case of infection.

Accordingly, the invention primarily provides a recombinant DNA, comprising two, 12–250 base pair long, inverted repeat nucleotide sequences with therebetween at least one nucleotide sequence which is derived from RNA virus which for its replication is dependent upon a viral RNA/RNA polymerase, said RNA virus derived sequence comprising at least cis elements for replication, but no gene that codes for RNA/RNA polymerase, and no gene that codes for viral coat protein.

To be employed, the recombinant DNA according to the invention must be incorporated in an expression cassette for a host to be transformed enabling transcription to take place in the host to form an RNA molecule with a panhandle structure.

Preferably, in a recombinant DNA according to the invention the RNA virus derived sequence contains both cis elements for replication and cis elements for transport.

The invention further includes such a recombinant DNA in which the RNA virus derived sequence also comprises cis elements for packing in coat protein and such a recombinant DNA in which the RNA virus derived sequence also comprises cis elements for translation. In the case of uses where these functions play no role, however, they are preferably absent, because they may have an adverse effect on the replication efficiency of the RNA formed by transcription. This holds in particular for the use of the invention for virus protection. This is one of the reasons why no gene that codes for viral coat protein may be present. Similarly, preferably no other unnecessary trans elements are present, such as a gene that codes for viral transport protein.

Accordingly, in the most preferable embodiments of the invention the RNA virus derived sequence, present in the recombinant DNA, corresponds to a stripped viral replicon which without outside help (such as infection with a helper virus) is incapable of multiplying and actively moving to other cells of the host, and which does not code for any viral protein. Such a substantially stripped viral replicon, however, exhibits in the presence of RNA/RNA polymerase a much more efficient replication than the complete viral genome. This is what makes the recombinant DNA according to the invention useful for the protection of the host against virus infections. Thus, when an infection of the genetically modified host by an RNA virus with the relevant RNA/RNA polymerase occurs, the number of RNA virus derived RNA molecules which are already present in the cells of the host will very rapidly increase and accordingly will increasingly appropriate the RNA/RNA polymerase at the expense of the multiplication of the infecting virus. Therefore the substantially stripped replicon has an important advantage over the complete viral genome in the battle for the available RNA/RNA polymerase. This advantage can be further increased when the RNA virus derived sequence incorporated in the genome of the host also contains cis elements for transport, in virtue of the fact that then also transport protein of the infecting virus, responsible for expansion of the infection to other cells of the host, is appropriated by the rapidly increasing RNA virus derived RNA molecules which are derived from the DNA incorporated.

A preferred embodiment of the invention, which concerns such use for protection of the host against viral infections, consists of recombinant DNA, in which between the two inverted repeat nucleotide sequences, in addition to the RNA virus derived sequence, also at least one nucleotide sequence is located which codes for a ribozyme which can cut viral RNA or mRNA.

When in the case of a viral infection by a virus which supplies the RNA/RNA polymerase in question, to be referred to hereinafter as a compatible virus, the RNA virus derived RNA present in the cells of the host under attack is rapidly multiplied, in this preferred embodiment the present amount of ribozyme with specificity for the infecting virus is also increased at the same time. This ribozyme takes care of an active destruction of the RNA of the infecting virus, or messenger RNA derived therefrom.

For further information on the structure and action of ribozymes, reference is made to Nature 334, page 197, 1988.

For further information on the formation and properties of substantially stripped replicons, reference is made to Perrault, Current Topics in Microbiol. and Immunol. 93, 1981, 152–209; Lazzarini et al., Cell 26, 1981, 145–154; Nayak, Ann. Rev. Microbiol. 34, 1980, 619–644; Barrett and Dimmock, Current Topics in Microbiol. and Immunol. 128, 1986, 55–84; "RNA genetics", 1989, E. Domingo et al., Eds., CRC Press, Boca Raton, Fla.; Strauss and Strauss, Current Topics in Microbiol. and Immunol. 105, 1983, 1–89. There they are designated as "defective interfering viruses/particles/RNAs". A highly defective replicon of an RNA virus can for instance be obtained by infecting a suitable host with bare viral RNA, isolating the replicated viral RNA and using it for a subsequent infection. Thus the need for coat protein is artificially eliminated, as a result of which deletion mutants are formed that do not contain a coat protein gene anymore. By further repeats of this procedure each time in the presence of a small amount of added RNA of this coat protein deletion mutant, also RNA can be isolated which does not contain an RNA/RNA polymerase gene anymore (due to the fact that the added RNA provides the necessary RNA/RNA polymerase, also RNA/RNA polymerase-deletion mutants undergo replication). Other methods of preparation, however, are also possible, such as a method in which cells or tissues with a very high dose of virus particles (100 or more per cell) are infected and RNA deletion mutants are isolated; or a method in which cells or tissues are infected with virus stocks, which contain satellite viruses or virusoids, and RNA deletion mutants are isolated; or a method in which a subgenome is isolated from an RNA virus with a bipartite or tripartite (or, more generally, polypartite) genome; or a method in which cells or tissues which produce a suitable RNA/RNA polymerase are infected with viral RNAs, optionally already partly deleted, and further deleted RNAs are isolated; or a method in which targeted genetic manipulations in the cDNA of a viral, satellite or virusoid RNA are performed.

The invention has important advantages over the previously proposed methods of protecting eukaryotic host organisms against virus infections, such as the formation of antisense viral RNA to block viral messenger RNA (see for instance Cuozzo et al., Biotechnology 6, 1988, 549–557), the formation of viral coat protein (see the cited article of Cuozzo et al., and Hoekema et al., Biotechnology 7, 1989, 273–279), or the formation of viral satellite RNA (see EP-A-0242016). The invention is subject to fewer limitations than the known virus protection methods. For instance, the invention is not limited to viruses of which a satellite virus is known, and is not limited to the incorporation of "sense" or "antisense" DNA (the RNA virus derived RNA formed by transcription may appropriate, both in the sense and in the antisense orientation, the trans functions for replication and possibly transport of the infecting virus). The invention also offers more possibilities for achieving greater effectiveness, such as the possibility of incorporating one or more ribozyme sequences. The invention combines a smallest possible burdening of the host and a highest possible protection for the host under infection-free conditions with an extremely fast and effective reaction, as soon as an infection by a compatible virus occurs, which reaction gives the host the required protection against the virus, exclusively at locations where that is necessary. The protection the invention offers is of a permanent nature because it is integrated into the genome of the host and, due to its being a minor burden on the host, exerts virtually no selection pressure. A simultaneous protection of the host against several different viruses is a real possibility of the invention owing to the fact that it constitutes virtually no extra burden on the host, i.e. the host need hardly use any energy (the transcription of the DNA inserted requires only very little energy, while in the preferred embodiment no translation into protein is involved). According to the invention the inverted repeat sequences may contain several different RNA virus-specific sequences (i.e. defective replicons of different RNA viruses), and/or several different ribozyme sequences (a ribozyme sequence which is specific for a first virus, a ribozyme sequence which is specific for a second virus, etc.). Naturally, however, these several different RNA virus-specific sequences and several different ribozyme sequences may also be incorporated each within two inverted repeat sequences of their own. In the known methods of virus protection such simultaneous protection against different viruses is not very well possible because the large amounts of entities providing protection, which must be produced continuously throughout the host to ensure effective protection constitute, due to their being a burden, a selective drawback of the host as compared with others of its type and/or are detrimental to its growth and development.

The above-mentioned properties of the recombinant DNA according to the invention are also responsible for its usability as regards methods of producing foreign proteins/peptides and RNAs using genetically modified, prokaryotic and particularly eukaryotic organisms. This concerns recombinant DNA according to the invention in which between the two inverted repeat nucleotide sequences, in addition to the RNA virus derived sequence, a non-viral nucleotide sequence is located which codes for one or more RNAS, and more particularly recombinant DNA according to the invention in which the RNA virus derived sequence comprises at least cis elements for replication and cis elements for translation and between the two inverted repeat nucleotide sequences, in addition to the RNA virus derived sequence, a non-viral nucleotide sequence is located which codes for one or more proteins/peptides.

In virtue of the above-mentioned properties of the recombinant DNA according to the invention the host produces at most a negligible amount of the foreign RNAs or proteins/peptides in the absence of RNA/RNA polymerase, while in the presence of RNA/RNA polymerase a sharp increase of the messenger RNA occurs, which results in a considerable production of the desired RNAs or proteins/peptides. This very strong production can moreover be induced at any desired moment, or be limited to specific tissues of the host by regulating the presence of the RNA/RNA polymerase accordingly.

An inducible production may for instance be accomplished by infecting the genetically modified host (or host cells in a cell culture, for instance) with a compatible virus at the desired moment. Normally, however, this method will not be preferable because it is laborious, the efficiency of the infection may be very variable, the infection mostly takes place at the expense of the host (a possible consequence being a breakdown of the desired product) and/or the use of the virus involves risks. Another, more attractive option, which may also be chosen to accomplish a tissue-specific production consists in a double transformation of the host, wherein the genome of the host is provided not only with the above described recombinant DNA according to the invention but also with recombinant DNA comprising genetic information for a viral RNA/RNA polymerase or an RNA/RNA polymerase construct in an inducible or tissue-specific expression cassette. For this purpose use can be made of known per se inducible (for instance by heat, UV irradiation, or chemicals such as salicylic acid) or tissue-specific (for instance patatin for expression in the tubers of potatoes) promoters.

The phrase "genetic information for an RNA/RNA polymerase construct" refers to gene constructions which may or may not effect coding for another RNA/RNA polymerase. A possible gene construction consists, for instance, of a mutation through which an internal facultative stop codon which may occur in genes coding for RNA/RNA polymerases, is replaced by a sequence not recognizable as a stop codon anymore. Another possibility is a gene construction which consists of a fusion of different RNA/RNA polymerase genes, naturally with the same above-mentioned option of using a mutation of an internal stop codon.

The invention is further embodied in eukaryotic or prokaryotic cells or organisms which through genetic engineering are provided with recombinant DNA according to the invention and optionally, through genetic engineering, are also provided with recombinant DNA comprising genetic information for a viral RNA/RNA polymerase or an RNA/RNA polymerase construct in an inducible or tissue-specific expression cassette.

The invention is further embodied in a method of protecting eukaryotic organisms, in particular plants, yeasts and fungi, against an RNA virus which for its replication is dependent upon a viral RNA/RNA polymerase by performing a genetic manipulation of the organism to be protected comprising incorporating into the genome of this organism recombinant DNA which in an active expression cassette comprises two, 12–250 base pair long, inverted repeat nucleotide sequences with therebetween a nucleotide sequence derived from RNA virus, this RNA virus derived sequence comprising at least cis elements for replication, but no gene that codes for viral RNA/RNA polymerase and no gene that codes for viral coat protein.

Preferably, in such a method the RNA virus derived sequence comprises both cis elements for replication and cis elements for transport. The RNA virus derived sequence may further also comprise cis elements for packing in coat protein and cis elements for translation.

Most preferably, in such a method, between the two inverted repeat nucleotide sequences, in addition to the RNA virus derived sequence, at least one nucleotide sequence is located which codes for a ribozyme which can cut viral RNA or mRNA.

The invention is further embodied in a method of inducibly producing one or more proteins/peptides by culturing a prokaryotic or eukaryotic organism, or cells of a prokaryotic or eukaryotic organism, which organism, through genetic engineering, is provided with (a) recombinant DNA which in an active expression cassette comprises two, 12–250 base pair long, inverted repeat nucleotide sequences with therebetween one nucleotide sequence which is derived from RNA virus which for its replication is dependent upon a viral RNA/RNA polymerase, this RNA virus derived sequence comprising at least cis elements for replication and cis elements for translation, but no gene that codes for viral RNA/RNA polymerase, and no gene that codes for viral coat protein, and (b) there being located between the two inverted repeat nucleotide sequences, in addition to the RNA virus derived sequence, a non-viral nucleotide sequence which codes for one or more proteins/peptides, and infecting the organisms or cells thereof with the virus.

Preferable, however, is a method of producing in an inducible manner or in a tissue-specific manner one or more proteins/peptides by culturing a eukaryotic organism, whose genome, through genetic manipulation, incorporates (a) recombinant DNA which in an active expression cassette comprises two, 12–250 base pair long, inverted repeat nucleotide sequences with therebetween a nucleotide sequence which is derived from RNA virus which for its replication is dependent upon a viral RNA/RNA polymerase, with this RNA virus derived sequence comprising at least cis elements for replication and cis elements for translation, but no gene that codes for viral RNA/RNA polymerase, and no gene that codes for viral coat protein, and (b) there being located between the two inverted repeat nucleotide sequences, in addition to the RNA virus derived sequence, a non-viral nucleotide sequence which codes for one or more proteins/peptides, as well as recombinant DNA which comprises genetic information for a viral RNA/RNA polymerase or an RNA/RNA polymerase construct in an inducible or tissue-specific expression cassette.

The invention is further embodied in a method of inducibly producing one or more RNAs, such as ribozymes, antisense RNAs and double-stranded RNAs, by culturing a prokaryotic or eukaryotic organism, or cells of a prokaryotic or eukaryotic organism, which organism through genetic engineering is provided with (a) recombinant DNA which in an active expression cassette comprises two, 12–250 base pair long, inverted repeat nucleotide sequences with therebetween a nucleotide sequence which is derived from RNA virus which for its replication is dependent upon a viral RNA/RNA polymerase, this RNA virus derived sequence comprising at least cis elements for replication but no gene which codes for viral RNA/RNA polymerase, and no gene which codes for viral coat protein, and (b) there being located between the two inverted repeat nucleotide sequences, in addition to the RNA virus derived sequence, a non-viral nucleotide sequence which codes for one or more RNAs, and infecting said organism or cells thereof with the virus.

More preferable, however, is a method of producing in an inducible manner or in a tissue-specific manner one or more RNAs, such as ribozymes, antisense RNAs and double-stranded RNAs, by culturing a eukaryotic organism, whose genome, through genetic engineering, incorporates (a) recombinant DNA which in an active expression cassette comprises two, 12–250 base pair long, inverted repeat nucleotide sequences with therebetween a nucleotide sequence which is derived from RNA virus which for its replication is dependent upon a viral RNA/RNA polymerase, this RNA virus derived sequence comprising at least cis elements for replication, but no gene which codes for viral RNA/RNA polymerase, and no gene which codes for viral coat protein, and (b) there being located between the two inverted repeat nucleotide sequences, in addition to the RNA virus derived sequence, a non-viral nucleotide sequence which codes for one or more RNAs, as well as (c) recombinant DNA which comprises genetic information for a viral RNA/RNA polymerase or an RNA/RNA polymerase construct in an inducible or tissue-specific expression cassette.

Thus the invention can be used broadly for the production in eukaryotes or cells of eukaryotes of one or more products such as proteins, oligo and polynucleotides, oligo and polypeptides, enzymes, antibodies, antigenic substances, antiviral compounds, anticancer substances, hormones, vitamins, medicines and pharmaceuticals, primary and secondary metabolites.

A further aspect of the invention is recombinant DNA comprising a nucleotide sequence which codes for a viral RNA/RNA polymerase or an RNA/RNA polymerase construct.

More particularly, according to a preferred embodiment, the invention provides such a recombinant DNA comprising the part of the nucleotide sequence shown in FIGS. 4a–4e that codes for a viral RNA/RNA polymerase, or constructs derived therefrom, such as a substitution mutant which has sequence TAT instead of the sequence TAG at the positions 656–658 according to the numbering used in FIGS. 4a–4e, and substitution mutants in which a part of the sequence shown in FIGS. 4a–4e is replaced by a corresponding part of another gene which codes for a viral RNA/RNA polymerase.

Such a recombinant DNA in which the nucleotide sequence which codes for a viral RNA/RNA polymerase or an RNA/RNA polymerase construct is located in an inducible or tissue-specific expression cassette constitutes yet another preferred embodiment of the invention.

The invention will now be explained in and by the following Examples.

Example I illustrates how tobacco plants can be protected against infection by TNV through transformation with a replicon derived from STNV. The replicon derived from STNV is a highly defective replicon which does not code for a protein and under infection-free conditions is produced only in a very limited amount, i.e. only a weak transcription of the DNA incorporated into the genome occurs. However, when the plant is infected with TNV, which codes for an RNA/RNA polymerase which is capable of multiplying the STNV derived replicon, massive reproduction of the STNV derived replicon occurs, irrespective of whether the STNV information is incorporated into the genome in sense or anti-sense orientation. As a result, the plant is protected against the infecting virus. This protection is much more effective when the DNA incorporated into the genome also comprises the information for a ribozyme which is directed against mRNA for TNV coat protein.

Example II illustrates how the invention can be used to accomplish an inducible production of a type-foreign protein. As a model for this purpose the beta-glucuronidase gene of *E. coli* was selected, which was fused with the initiation codon of the STNV coat protein. In the example given the expression was induced by infecting the transformed tobacco plants with TNV.

Example III describes the isolation of the replicase gene of TNV and the construction of a plasmid pSPTNV rep-1, which contains this replicase gene.

Example IV describes expression experiments in which amplification of the messenger RNA by contact with the TNV replicase was effected. The viral replicon contained as foreign DNA a fusion of a part of the gene which codes for the viral coat protein of STNV, and the chloramphenicol acetyl transferase (CAT) gene of *E. coli*.

EXAMPLE I (a) Recombinant plasmids

Starting from the plasmid pSTNV-413 described by Van Emmelo et al. in Virology 157, 480–487 (1987), a number of new insertion mutants were constructed. The starting plasmid was linearized with RsaI, which has 9 cutting sites in the STNV genome, by incubating at 28° C. with 0.1 μg enzyme per μg DNA for 15 min. Ligation with the same 14-mer linker as described by Van Emmelo et al: 5' TCCATGGGAATTCT 3' led, among other things, to the insertion mutant pBR STNV N162, which contains the linker with the NcoI site at the 5' end at position 162 of the STNV genome.

From this insertion mutant and the insertion mutants pBR STNV N198, N322 and E531, already described by Van Emmelo et al., all of which contain the reading frame interfering insertion of the above-mentioned 14-mer linker in the gene coding for coat protein, mutants with a recovered reading frame were constructed. To that end the 14-mer insertion was converted into an 18-mer insertion by cutting with NcoI, filling in the single-stranded ends with Klenow enzyme in the presence of the 4 dNTP's, and religation of the plasmid. Thus the 14-mer insertion is converted into the following 18-mer insertion: 5' TCCATGCATGGGAATTCT 3', in which the NcoI site (CCATGG) is replaced by an NsiI site (ATGCAT). Thus the insertion mutants pBR STNV N164, N200, N324 and E533 were obtained which theoretically code for a coat protein which is increased by 6 amino acids.

Further the double insertion mutant pBR STNV N164N843 was constructed by isolating from pBR STNV N843 the EcoRV fragment of bases 198 to 962 in the STNV genome and substituting it for the corresponding EcoRV fragment of pBR STNV N164.

From the 18-mer insertion mutants pBR STNV N164 and N200 the mutants pBR STNV S164 and S200 were constructed by inserting an additional linker of 18 bases as NsiI fragment in the NsiI site of the 18-mer insertion:
in S164: 5' TCCATGCAATCGAGGGTAGGCATG-CATGGGAATTCT 3'
in S200: 5' TCCATGCATGCCTACCCTCGATTG-CATGGGAATTCT 3'

These mutants have an insertion of 36 bases and code theoretically for a shorter coat protein as a result of a reading frame mutation in the case of S164 and for a coat protein with 12 extra amino acids in the case of S200.

By inserting the same 18-mer in the unique NsiI site at the end of the coat protein gene (base 613), the mutant pBR STNV S613 was obtained.

At the location of the RsaI site at position 162 a linker of 30 bases was inserted in a similar way as described hereinabove for the 14-mer linker. In the reading frame that is formed thus this linker codes for the neuropeptide bradykinin: 5' GCGGCCGCCCGGGTTTAGTCCTTTTAGGTT 3'
ArgProProGlyPheSerProPheArg This insertion mutant was designated pBR STNV Brad.

From pBR STNV N164 the deletion mutant pBR STNV D1 was made by a deletion of the NsiI fragment of 167 to 631. The genome of this mutant has a length of 793 bases as compared with 1239 for wild type STNV.

For expression studies in *E. coli* the various STNV constructions were transcloned as PstI fragment into pPLC 2820. The restriction enzyme PstI cuts precisely at the end of the poly GC regions which flank the 5' and 3' ends of STNV. These constructions in pPLC2820 are designated as pPLC, followed by the name of the STNV mutant, further followed by .1 when the 5' end of the STNV genome adjoins the pL promoter of pPLC 2820, or by .2 when the 3' end adjoins the promoter. Thus the plasmid pPLC STNV N164.1 is the plasmid with the STNV mutant N164 cloned into pPLC 2820, with the STNV mutant being inserted into the plasmid such that upon transcription by pL the equivalent of the positive-strand genomic RNA of STNV is made as mRNA.

The STNV mutants cloned as PstI fragment into pPLC 2820 are preceded at the 5' end by a unique BamHI site and at the 3' end followed by a SalI site. Since neither STNV, nor the mutants derived therefrom, contain a BamHI or a SalI site, the different constructions can be transcloned as BamHI/SalI fragment into pPCV 520 (FIG. 1) behind the plant promoter pTR1'. The plasmids thus obtained are designated as pPCV, followed by the name of the STNV mutant, further followed by .1 when the 5' end, and by .2 when the 3' end of STNV is turned towards the promoter pTR1'. The pPCV derivatives were used for transformations of tobacco plants as part of a binary vector system, as described by Hoekema et al. in EMBO Journal 3, 2485 (1984) and by De Framond et al. in Mol. Gen. Genet. 202, 125 (1986). The plasmids derived from pPCV 520 functioned as the T-plasmid (i.e. the plasmid that contains the T-DNA which is integrated into the genome of the plant through the transformation). The most important properties of pPCV 520 (see FIG. 1) are:

ColE1 replication in *E. coli*, which makes it suitable for use in all current *E. coli* strains and which makes it a multicopy plasmid (efficient DNA preparation and clone analysis)
bacterial resistancies against the antibiotics ampicillin and chloramphenicol the P-type replication origin of pRK2 is active in *E. coli* and in Agrobacterium, provided that the RK2-gene trfa is expressed (in Agrobacterium, moreover, selection is necessary for stability)

the P-type transfer origin of pRK2 permits an efficient transfer of the plasmid from strains in which the pRK2-genes tra1, tra2 and tra3 are expressed (for *E. coli* this is the case for the strain SM10 and for Agrobacterium for strains which contain the plasmid pMP90RK)

the border sequences of the T-DNA flank all elements of the vector which are important in plants the NPT-II kanamycin resistance gene under the control of the plant promoter pTR2' permits selection of transformed plants the octopine synthase gene in the T-DNA makes it possible to confirm the transformation of kanamycin-resistant plants using octopine synthesis the constitutive plant promoters pTR1' and pnos, are followed by the unique restriction sites for SalI and BamHI and for BglII and BclI, respectively and by the polyadenylation sequences of the T-DNA genes 7 and 4, respectively back cloning of T-DNA sequences from transformed plants is simplified by the pBR322 oriV and ampicillin resistance in the T-DNA.

The T-plasmid pPCV 520, therefore, can replicate both in *E. coli* and in Agrobacterium. The cloning steps for the introduction of the STNV mutants into this vector can be performed in *E. coli*. Then, by conjugation, the vector is transferred from *E. coli* SM10 into the Agrobacterium strain GV3100 (pMP90RK), which is used for the plant transformations. The plasmid pMP90RK (FIG. 2; see Koncz and Schell, Mol. Gen. Genet. 204, 1986, 383–396) functions as virulence plasmid. It is derived from the nopaline Ti-plasmid pGV3100 by (1) a combined deletion and insertion mutagenesis, leading to a complete deletion of the T-DNA and to the incorporation of a gentamycin resistance gene (the construction thus obtained is designated as pMP90), and (2) the insertion of a fragment of the P-type plasmid pRK2013 with thereon the genes for kanamycin resistance, the genes acting in trans for transfer and replication of P-type plasmids and the P-type origin of transfer (Figurski and Helinski, PNAS USA 76, 1648 (1979)). The most important properties of this plasmid pMP90RK (see FIG. 2) are:

a stable replication only in Agrobacterium compatibility with P-type plasmids it codes for all Ti-virulence functions which are necessary and sufficient for the integration of the T-DNA into the genome of plants during transformation it contains gentamycin and kanamycin resistance genes as genetic markers which are easy to select it complements transfer and replication of P-type mutants by the expression of the pRK2-genes tra1, tra2, and tra3 and trfa it conjugates very efficiently owing to the P-type oriT.

(b) Techniques

The transformation of plants (tobacco SR1) was according to the leaf segment method, described by De Block et al. in EMBO Journal 3, 1681 (1984) and by Horsch et al. in Science 223, 496 (1984). The procedure was as follows:

by incisions with a scalpel tobacco leaves are wounded and the freshly wounded leaves are incubated for 48 h with a 1/50 dilution of a freshly grown culture of the transforming Agrobacteria. This is conducted in liquid MS-plant medium (Murashige and Skoog medium, Gibco)

then the leaf fragments are washed twice for 12 h in liquid MS-medium to which claforan (500 μg/ml) is added (claforan is an antibiotic which acts only against bacteria)

then the leaf fragments are incubated on solid MS-medium (+0.8% agar) to which cytokinin (6-benzyl-aminopurine or BAP, 1 mg/l) and auxin (α-naphthalene acetic acid or NAA, 0.1 mg/l) are added in a ratio which promotes shoot formation at the location of the wounds, kanamycin (100 μg/ml) for the selection of transformed shoots and claforan for the further selection against the transforming Agrobacteria after 4 to 10 weeks transformed shoots grow on this medium and, when they are sufficiently developed, can be transferred to hormone-free medium where they can develop to normal plants with roots.

Callus induction was performed on sterile leaf and stem fragments. For that purpose the fragments were incubated on solid MS-medium (+0.8% agar) to which the cytokinin BAP (0.5 mg/l) and the auxin NAA (1.0 mg/l) were added in a concentration and ratio which promote callus growth.

For octopine tests small particles of plant tissue (about 50 mg) were incubated overnight in a solution of 100 mM L-arginine and 50 mM pyruvate dissolved in liquid MS-medium. After incubation the liquid was removed and the tissue was washed in MS-medium. Then the plant fragment was crushed and centrifuged, and 3 to 5 μl of the extract was separated by paper electrophoresis. This was conducted on Wattman 3 MM paper, in a solution of 15% HAc, 5% HCOOH and 80% $H_2O$. Octopine spots on the paper were made visible under UV lighting after a staining reaction with a fresh mixture of 1 part 0.02% phenanthreen-quinone in 95% EtOH and 1 part 10% NaOH in 60% EtOH.

Plasmid infections of cowpea were performed to investigate the infectivity of the STNV mutants. To that end cowpea was inoculated with a mixture of TNV helper virus and chimeric plasmids according to the method described by Van Emmelo.

Northern analyses were performed essentially in the manner described by Van Emmelo. For the analysis of the transformed plants single- and double-stranded RNA were not separated by LiCl precipitation for gel electrophoresis. Besides denaturing glyoxal agarose gels, denaturing formamide agarose gels were used, as described by Lechrach et al in Biochemistry 16, 4743 (1977) and by Maniatis et al in Molecular Cloning: a laboratory Manual, Cold Spring Harbor Laboratory, Cold Spring Harbor, N.Y., USA. In this method the RNA samples are first denatured at 55° C. for 15 min in a mixture of 50% formamide, 17.5% formaldehyde, 20 mM morpholino propane sulfonic acid (MOPS) (pH 7.0), 5 mM NaAc and 1 mM EDTA (pH 8.0). Gel electrophoresis was conducted in a 1.2% agarose gel in 20 mM MOPS (pH 7.0), 5 mM NaAc and 1 mM EDTA (pH 8.0) as a transporting buffer. The further treatment of the samples for blotting and hybridization was carried out in the manner described by Van Emmelo.

Western analyses for detecting TNV and STNV coat protein were performed as follows. Infected leaves were harvested after two days and, using a potter, were ground at 4° C. in 1 volume part PBS (PBS=0.13 M NaCl, 10 mM sodium phosphate buffer pH 7.4) which contained 100 μg/ml PMSF. Cell residues were removed by centrifugation and the proteins were precipitated with trichloroacetic acid (TCA, final concentration 10%). The precipitate was washed in ethanol, ethanol ether (1:1) and ether, dried and resuspended in 1× Laemmli-buffer (Nature 227, 680–685, 1970). Fractions thereof were separated on a 10% PAG by electrophoresis, and via electrotransfer for 90 min at 0.5 A transferred to Pall-biodyne filter in a transfer buffer (1 mM sodium acetate, 5mM MOPS pH 7.5 in 20% ethanol). The filter was blocked overnight in PBS which contained 10% low-fat milk powder and was incubated with anti-STNV coat protein serum of rabbits, diluted 1:200 in PBS, 2% low-fat milk powder at room temperature for 1 h. The filter was washed four times with PBS, 0.1% Triton-X-100 and incubated with anti-rabbit alkaline phosphatase labeled antibodies from goats, diluted 1:250 in PBS, 2% low-fat milk powder. After washing out non-bound antibodies, a staining reaction was carried out using Nitro Blue Tetrazolium (NBT) and 5-bromo-4-chloro-3-indolyl phosphate (BCIP), under the conditions as indicated by the producer (Promega Biotec).

(c) Experiments and results (c1) expression studies in *E. coli* NF1

A number of pPLC STNV plasmids with the modified STNV genome in the sense orientation (the .1 constructions) and the plasmids pPLC STNV N164.2 and Brad.2 (with the antisense orientation) were transformed in *E. coli* NF1. This strain has a ts (temperature-sensitive) mutation of the c1 repressor gene of pL, by which the pL promoter is repressed when the bacteria are cultured at 28° C. At a temperature of 42° C. the repressor is unstable and the promoter yields pL transcription.

Using Western blotting the synthesis of coat protein was investigated, i.e. the presence or absence of coat protein and the difference in size of the proteins encoded by the different STNV mutants. The results are summarized in Table 1. It reveals that the STNV mutants with a reading frame mutation (+14 or +36 bases) yield a shortened coat protein whose length is greater according as the insertion is located further towards the 3' end the insertion mutants with a recovered reading frame (+18, +30 or +36 bases) yield a larger coat protein than the wild type, while the mutual mobility (+18>+30>+36) corresponds to the higher molecular weight, which is expected on the basis of the number of added amino acids (+6, +10 and +12)

only the plasmids in which the modified STNV is inserted in the .1 orientation relative to the promoter, yield coat protein.

(c2) plasmid infections

Unless indicated otherwise, for the plasmid infections pBR STNV plasmids were used. The plasmid pSTNV 413 was used as a positive control in the infections to allow correlation of the various experiments. As a negative control pBR STNV N843 was used, which had been previously established as replication-deficient. When the signals after the primary infection were very weak or absent, secondary infections with RNA extracts were performed on cowpea to obtain clearer RNA and protein signals.

In the analysis of the inoculated leaf material the synthesis of coat protein was assayed by Western blotting and that of RNA by Northern blotting. For the RNA single- and double-stranded RNA were separated and their presence was determined separately. The results are also summarized in Table 1. It reveals that dsRNA (double-stranded RNA) is present in all mutants with an insertion in the coat protein gene and is absent only in the mutants with an insertion at position 843 coat protein and normal amounts of ssRNA (single-stranded RNA) are only found in the mutants N164, N200 and Brad in the insertion mutants in which no coat protein is found, the plants also contain much less ssRNA the coat proteins which are produced for the mutants N164, N200 and Brad in the plants and in *E. coli* NF1 are of equal length.

By hybridization with a strand-specific probe (with an SP6 RNA transcript of STNV or with the suitable single-stranded linker for the different mutants) it was established that the ssRNA isolated in the different infections is positive-strand and accordingly corresponds to the genomic RNA (also when no coat protein, no particles and only small amounts of ssRNA are present).

Besides the various pBR STNV plasmids, for the mutants N164.1, N164.2, Brad.1 and Brad.2 also the pPLC and pPCV plasmids were used for plasmid infections, with the same results.

(c3) expression of STNV mutants in transformed plants

Transformations of tobacco SR1 were performed with the following T-plasmids:

pPCV 520 pPCV STNV N164.1 and .2 pPCV STNV N164N843.1 and .2 pPCV STNV Brad.1 and .2

Transformation with pPCV 520 was performed as a check on the transformation experiment itself. Using the infective STNV mutant N164 with a linker insertion in the coat protein gene enables both the coat protein (+6 amino acids) of the mutant and the RNA (by hybridization with the specific linker) to be distinguished from the wild type in the analysis of the results. The mutant N164N843 was selected as replication-deficient genome. In this mutant the insertion N164 is used to identify the coat protein and to distinguish it from the wild type, while the two inserted linkers enable identification of the RNA. The mutant STNV Brad was used for transformation to establish whether the expression of the fusion protein between the STNV coat protein and the bradykinin is amplified by an infection of the transformants with the helper virus TNV. The transformed plants are designated by SR1, followed by the identification of the STNV mutant and further followed by a number used to identify the independent transformants with the same mutant.

The kanamycin resistant plants which after transfer to hormone-free medium with kanamycin developed roots in a normal manner, were grown up for further investigation. Of these plants also callus cultures were produced to enable confirmation of the transformation of the kanamycin resistant plants by octopine tests. The point is that the octopine synthase gene in the T-DNA of pPCV 520 is under the control of a tissue-specific promoter of T-DNA gene 5, which is expressed only in stem fragments (very weakly) and in callus tissue, so that the octopine tests are preferably performed on callus tissue. More than 90% of the kanamycine resistant plants proved indeed to be transformed.

Transformed plants were obtained under sterile growth conditions. For TNV infection small top shoots were first allowed to grow roots in vitro and then transferred to potting soil to be further cultured under greenhouse conditions. The plants were allowed to develop further and infected with TNV when they were sufficiently large. The mechanical infection was performed with a fresh TNV-inoculum, isolated from tobacco SR1. After 72 h the infected leaves were harvested, frozen in liquid nitrogen and preserved at −70° C. Besides the TNV infected leaves, non-infected leaves of the same plant were harvested and analysed.

The presence of STNV RNA and coat protein in the various samples were determined by Northern and Western blotting, respectively, Table 2 summarizing the results. The Table reveals that

- TNV infection of plants transformed with STNV under the control of a constitutive plant promoter and flanked by inverted poly-GC-regions leads to the replication and expression of the STNV genome and to the formation of STNV particles
- the insertion mutant N164N843 characterized as replication-deficient replicates normally in transformed plants
- the STNV construction with a fusion between the coat protein and the bradykinin, after infection with TNV, yields replication of the mRNA and amplified synthesis of the fusion protein
- the detected STNV RNA according to the hybridizations with the various linkers corresponds to the mutant genome which the plants had been transformed with
- the plants with the STNV genome in the .2 orientation, i.e. they produce the anti-sense mRNA, after infection with TNV also yield STNV replication and expression, without observable differences with the .1 plants
- the differences in the intensity of the RNA and protein signals do not correlate with the type or the orientation of the mutant STNV genomes, but are typical of the individual character of independent transformants with the same genome.

Owing to the fact that for the assessments only 10 mg plant material was used, neither RNA nor coat protein could be detected in the transformed plants without TNV infection.

Repeat experiments all produced qualitatively and quantitatively similar results. Significant variations were observed only for the efficiency of the TNV infection, depending on various factors such as age and the differentiation level of the infected plants, the quality of the inoculum, the temperature, the humidity, etc. When the TNV infection was insufficiently strong, only weak RNA signals and no protein signals were obtained. With a proper TNV infection, on the other hand, much stronger STNV signals were obtained from STNV formed plants than in the case of the plasmid infections of transformed plants. On the basis of the intensity of the signals obtained in Western analysis, the amount of coat protein could be estimated at about 100 ng in a sample prepared from 10 mg leaf material. Taking into account the limitation of the synthesis of the STNV coat protein to the region of the necrotic lesions where TNV is also present, which lesions constitute only about 5% of the total leaf, it can be calculated from this that the STNV signal constitutes about 0.02% of the total, wet leaf weight or about 0.5% of the dry weight. This relatively large amount of protein is formed in only 3 days, after expression is induced by TNV infection.

The results with the STNV N164 and Brad mutants reveal that the 18-mer insertion and the fusion with bradykinin do not influence the replicability and the expression of the STNV-RNA. This proves that the coat protein can be replaced in whole or in part without adverse effects on replicability and expression of the STNV-RNA. See also Example 2, to follow hereinafter.

Quite unexpectedly, it turned out that the mutant N164N843, unlike in the case of the plasmid infections, replicated normally in transformed plants (by linker hybridization it was proved that the 14-mer insertion at position N843 was indeed present in the detected and replicated RNA). Apparently, the absence of ssRNA and dsRNA in plasmid infections with STNV N843 is not the result of a deficient replication. Further it appeared that replication of the STNV-RNA is not dependent upon the presence or absence of STNV coat protein or STNV particles. Since in these mutants the spread of STNV infection from cell to cell occurs in a normal manner, only the viral RNA (ds or ss) can be responsible for this. However, the different behavior of the mutant N843 in plasmid infections and in transformed plants can be explained by assuming that this mutation prevents the normal cell to cell spread of the STNV infection by RNA. In plasmid infections this mutant is not infective. In transformed plants, however, the STNV-mRNA occurs in all cells and spreading is not necessary to obtain normal levels of replication. In addition to structural elements for replication, therefore, the STNV-RNA also contains structural elements which are necessary for cell to cell transport. Probably a TNV-encoded protein plays an active role here.

In the transformants where STNV is inserted in the .2 orientation relative to the plant promoter, the anti-sense or negative-strand RNA is formed as messenger RNA. Previous attempts to initiate an STNV infection with the negative-strand RNA using SP6-transcripts had failed. In transformed plants this appears to be possible after induction with TNV, and is as efficiently as with the STNV .1-transformants. It is therefore possible to repress completely the expression of a gene during the entire growth phase of the plant due to the fact that only the anti-sense messenger RNA of a protein is produced, and to limit expression to the period when the helper functions for replication are present, while a strong expression can be obtained in a short time by replication and amplification of the anti-sense to produce sense RNA. Especially for the synthesis of toxic products it may be of great importance to repress entirely their expression during the growth period so as to prevent a negative influence on the development of the plants.

(c4) In vivo deletions

In plasmid infections with STNV, wild type and mutants, often secondary infections were performed to obtain clearer signals for RNA and protein in the analysis of the mutants. These infections were done with total RNA (ds and ss) from these plants, while both the STNV and the TNV infection were transferred. By thus continuing the same infection three to four times consecutively, deletion mutants of the STNV could be isolated. Northern blotting made the RNA of these mutants visible as clear, faster migrating discrete bands. In different infection lines different mutants were formed independently of each other, the length of the replicating RNA varying from about 600 to 900 bases. It appeared that when in an infection line such deletion mutants of STNV formed, the original wild type genome disappeared after 1 or 2 further infections. Also, in existing and fairly large deletion mutants, additional deletions could lead to the formation of smaller derivatives. Upon continuation of such an infection line, the larger mutant disappeared. Generally it was established that sufficient repetition of these infections led to the formation of STNV deletion mutants with a genome of about 600 bases. Western blotting demonstrated that the STNV deletion mutants no loaner code for the coat protein. By hybridizations with different fragments of the STNV genome it was determined that the deletion is located in the 5' end region of the genome.

Elements which seem to play a role in the formation of these deletion mutants are:

- the lack of a coat protein due to which the mutants are no longer encapsulated and all the positive-strand RNA in the infected cells remains available for replication and possibly for the spread of the infection
- since larger deletions (without coat protein gene) evolve further to even smaller genomes, it can be assumed that the mutants replicate faster and undergo a more efficient infection according as they are smaller (invariably more STNV-RNA is found in the deletion mutant infected plants than in the wild type infected plants, and the amount increases when the mutants become smaller).

The most important observation in the performance of these deletion mutants, however, is their strong interference with the TNV helper virus. When in an RNA infection line STNV deletion mutants are formed, the amount of TNV decreases very sharply. This decrease is so strong after 1 or 2 further infections that without addition of fresh TNV or TNV-RNA to the RNA inoculum no new infections can be carried out any more. Accordingly, the STNV mutants which are formed here by the unnatural RNA inoculations appear to yield a very efficient repression of the TNV infection.

Accordingly the in vitro constructed deletion mutant STNV D1 DNA, as described under Example I(a) was infected on cowpea by plasmid infection in the presence of TNV. When this deletion mutant was propagated further by RNA inoculation in accordance with the in vivo deletions, its replication proved to be more efficient than that of the original N164 mutant. Like the RNA mutants that form in vivo, STNV D1 RNA represses the TNV replication. This is evidenced by a lower infectivity of an RNA inoculum from these plants.

The deletion mutant STNV D1 constructed in vitro was also transformed to tobacco SR1 to investigate whether the influence on TNV replication would lead to protection of the transformed plants against TNV infection. To determine the effect of the expression of the RNA of the STNV deletion mutant on the development and the course of the infection with TNV, for comparison the following plants were grown under identical conditions as much as possible, infected and further observed:

SR1

SR1 STNV N164N843.1/1 and /2, with strong and weak expression of STNV, respectively

SR1 STNV D1.1/1

In each of these plants 4 leaves were infected which had a development and differentiation of a similar nature. For the infection a fresh inoculum, prepared from TNV-infected cowpea, and a frozen inoculum from infected tobacco were used, both diluted 1/1 (designated inoculum 1 and 3, respectively) and 1/10 (inocula 2 and 4). Two half leaves of the various plants were infected with each of the 4 inocula at similar locations; these leaves were designated a, b, c, and d from the bottom to the top. Thus the following combinations were made: a1 and a2, b3 and b4, c2 and c4, and d1 and d3.

After 72, 96 and 170 h the development of the infection was observed and photographically recorded. Also, after 96 h particles were taken from each leaf and photographed under UV light to investigate the hypersensitivity response of the plants. After 96 h the half leaf of each plant with the best developed lesions (b3) were harvested. A part of it was frozen and retained for further analysis of RNA and protein composition. The other part was used for the preparation of an inoculum to infect cowpea leaves. For each of the tobacco plants 4 cowpea leaves were infected:

with an extract from one single lesion (1 leaf)

with an extract from 200 mg leaf tissue (2 leaves)

with an 1/5 dilution thereof (1 leaf)

The photographs (not shown) revealed that a great difference occurred in the development of the TNV infection in the various tobacco plants. The most important differences were:

the number of lesions on the various leaves differed according to the inoculum used (3>4>1>2), with a minor difference between the plants (SR1>SR1 N164N843.1/1 and /2>SR1 D1.1/1)

the lesions in SR1 D1.1/1 are clearly smaller than in the other plants; tobacco SR1 and N164N843.1/1 differ most, while N164N843.1/2 is in-between. The differences in size of the lesions on one and the same plant depending on the leaf (a>b>c>d) are normal and are associated with the stage of development of the leaves particularly after 170 h it is clear that fairly large portions of the infected leaves of SR1 and SR1 N164N843.1/1 necrotize completely, while the corresponding leaves of D1/1, it is true, show lesions, but otherwise remain normally green UV light makes visible fluorescent rings and stains which are a result of the hypersensitivity reaction of the plant. Due to this reaction infected parts of the plant are isolated by a ring of tissue which leads to these parts dying off. For SR1 D1.1/1 these parts are much smaller than for the other plants. This points to a less extensive infection of the leaf.

After 96 h, from each plant a part of the half leaf b3 was used to prepare an inoculum for the cowpea leaves to be subsequently infected with. After 72 h very clear differences in the extent of infection of the cowpea leaves were to be observed. The plant which had been infected with the inocula prepared from the deletion plant yielded lesions but each of the leaves was still green. After 72 h the necrotization of the other plants had progressed much further and several of the leaves were so infected that they were already withered completely and almost fell off.

To compare the amount of TNV-RNA in the various plants, it was attempted to demonstrate the presence of TNV ds and ssRNA in EtBr-stained agarose gels. The amount of TNV-coat protein was determined by Western blotting. It was found that the amount of TNV-RNA in SR1 D1.1/1 was smaller than in the other plants. The amount of coat protein in SR1 D1.1/1 was about 20 times lower than that in tobacco SR1, while the amount in SR1 N164N843.1/1 and/2 was in between the two. The secondarily infected cowpea leaves were also examined for the presence of TNV-RNA and this yielded the same picture as in the tobacco plants.

In the case of grand-scale infection of the plant or portions thereof, the presence of RNA of STNV deletion mutants leads to no, less, or delayed complete necrotization and loss of the infected portions. In infected but protected plants much less TNV is produced, which has an inhibitory effect on the spread of the infection to other plants. The total protective effect is accomplished with the synthesis of a negligible amount of RNA. Only when the infection actually occurs do the virally encoded replication functions produce high and protection-yielding concentrations of deletion-RNA. moreover this occurs only in the infected cells, so that the energy burden on the plant is negligible.

EXAMPLE II

In the experiments described herein use was made of the glucuronidase gene of *E. coli*, because the enzyme glucuronidase retains its activity as fusion protein, no plant glucuronidase activity is known and the enzyme activity can be detected in a quantitative and very sensitive manner. The glucuronidase (GUS) gene (uidA) used in the various constructions was isolated as PstI-EcoRI fragment from the plasmid pRAJ255, described by Jefferson et al in PNAS 83, 8447–8451 (1986). To enable the GUS gene to be inserted in the desired position and in the proper reading frame in the STNV-cDNA, the following adjustments were carried out:

by substitution of the 1549 bp ScaI-NdeI fragment of the plasmid pPLC 321 by the corresponding fragment of plasmid pPLC 2820 (which leads to the removal of the PstI site in the ampicillin gene) the plasmid pPLC 322 was constructed by insertion in the unique NcoI site of pPLC 322 of a synthetic linker of the structure:
CATGGCTAGCAGCTGCAGGAATTCATGCATC
CGATCGTCGACGTCCTTAAGTACGTAGGTAC
the plasmid pPLC 323 was obtained by cloning the PstI-EcoRI fragment containing the GUS gene from pRAJ255 into pPLC 323, the plasmid pPLC GUS1 was obtained, in which the GUS gene is flanked by two NcoI cutting sites in pPLC GUS1 a unique PstI cutting site is located right before the coding portion of the GUS gene; by cutting the plasmid with PstI and removing the 4-base long 3'-overhanging ends by means of T4-polymerase, the plasmid pPLC GUS dPst1.1 was obtained, which still contains the two NcoI sites.

The insertions of the GUS gene were performed in the following STNV plasmids:

pPLC STNV N160.1 and .2 (the sense and the anti-sense orientation relative to the pL promoter), with a complete STNV genome, provided with a 14 bp linker insertion at position 160. The inserted linker contains a unique NcoI cutting site by linker mutagenesis at position 28 of the STNV genome the base A was replaced by the base C, which leads to the formation of an NcoI cutting site which overlaps the initiation codon of the coat protein gene. The introduction of this mutation into STNV N160 yielded the plasmids pPLC STNV N160Nco1.1 and .2. After cutting with NcoI and ligation the 134-bp long NcoI fragment of these plasmids can be deleted, which leads to the plasmids pPLC STNV dNco1.1 and .2.

The insertions of the GUS gene in STNV were accomplished as follows:

the GUS gene was cloned as NcoI fragment from pPLC GUS1 into pPLC STNV N160.1 and .2. In the proper orientation this yielded the plasmids pPLC STNV GUS.1 and .2, the GUS gene being fused in the proper reading frame with the 5'-portion of the STNV coat protein. Translation of the fusion protein stops at the location of the stop codon of the GUS gene, the 3'-portion of the coat protein is not translated. In fact these constructions represent the pure insertion of the GUS gene in STNV the GUS gene was cloned as NcoI fragment from pPLC GUS dPst1.1 into the NcoI cutting site of pPLC STNV dNco1.1 and .2, which yielded the plasmids-pPLC STNV GUS dNco1.1 and .2. The insertion was such that the AUG initiation codon of STNV was retained, followed by 7 codons from the synthetic linker and adjoining the initiation codon of the GUS gene in the proper reading frame. Translation stops likewise at the location of the stop codon of the GUS gene and thus provides the glucuronidase with 8 additional amino acids at the amino-terminal end the plasmids pPLC STNV GUS.1 and .2 and pPLC STNV GUS DNco1.1 and .2 were cut with NsiI (this restriction enzyme cuts right behind the GUS gene and right at the end of the coat protein gene) and ligated. Thus an NsiI fragment of 468 bp was deleted and the plasmids pPLC STNV GUS dNsi1.1 and .2, and pPLC STGUS.1 and .2 were obtained, respectively. These last two plasmids pPLC STGUS.1 and .2 contain the constructions in which the coat protein gene is entirely substituted by the GUS gene.

Starting from the pPLC plasmids the constructions STNV GUS and STGUS were transcloned as BamHI-SalI fragment in the plant vector pPCV 520, behind the pTR1' promoter. In the process the orientation relative to the promoter is reversed so that, for example, the plasmid pPCV STGUS.2 is formed from pPLC STGUS.1.

Expression in plants was tested by plasmid infections of cowpea with the various STNV-GUS constructions. For that purpose the plasmids pPLC STNV GUS.1 and .2, and pPCV STNV GUS.1 and .2 were used. Cowpea leaves were infected with plasmid and helper virus and harvested 3 days after inoculation. A freshly harvested leaf was incubated overnight in a 2 mM solution of X-Gluc (5-bromo-4-chloro-3-indolyl-beta-D-glucuronic acid) in 40 mM phosphate buffer, pH 7.4, at 37° C. Then the leaves were fixated in glutaraldehyde (6 h) and decolourized with an ethanol series (from 30 to 95%). Conversion of the X-Gluc by the glucuronidase leads to the formation of an insoluble blue precipitate.

With the four above-mentioned plasmids four independent infection series were performed on cowpea, in two cases of which a localized blue reaction was observed in the incubated leaves. With pPLC STNV GUS.1 a blue edge was observed at the location of a lesion. Microscopic examination of the fixated material revealed that the stain reaction was localized in the plant cells which were located right at the edge of the lesion. With pPLC STNV GUS.2 the reaction was visible in the form of a 0.3 mm spot. A microscopic examination could not establish whether the reaction was intracellular, because the plant cells had been damaged too severely by infection through bacterial contamination during the incubation with the substrate. However, because the blue colour was preserved during fixation, decolourizing, embedding and cutting, it can be assumed with fairly great certainty that the reaction was plant-specific.

Further, also a transformation of tobacco was performed, using the T-plasmids pPCV STNV GUS.1 and .2. For both constructions transformants were obtained. GUS tests before and after TNV infections of the grown transformants proved to meet the expectations.

EXAMPLE III

Isolation of the gene for replicase of Tobacco Necrosis Virus

Used as starting material was Tobacco Necrosis Virus (TNV) Kassanis strain A and serotype A, which is capable of multiplying Satellite Tobacco Necrosis Virus (STNV) SV-1 (SV-A serotype). This strain was obtained from Dr. Wieringa Brants, Phytopathologic Laboratory, Baarn, the Netherlands. TNV, free of STNV, was obtained as described by Van Emmelo et al., Virology 157, 480–487 (1987).

TNV virus was increased in Phaseolus leaves (Vigna unguiculata, cowpea), by infection with virus and carborundum. Genomic RNA was prepared from purified TNV particles and converted into cDNA with AMV reverse transcriptase (Boehringer) using random primers. The second strand synthesis was performed by *E. coli* DNA polymerase I (Klenow fragment) and RNAaseH (Boehringer) according to the method of Gubler and Hoffman (Gene 25, 263–269, 1983). Then T4 DNA polymerase was added to blunt the ends. After cloning into plasmid pSP64 (Promega), cut with SmaI with simultaneous treatment of the ends with phosphatase, the clones were (transferred) to *E. coli* MC1061 by transformation and the colonies were (tested) by colony-hybridization with fragmented $^{32}P$ ds TNV RNA.

Subgenomic ssRNA prepared from Phaseolus leaves infected with TNV was used for Northern hybridization with the selected TNV clones. The lengths of these subgenomic RNAs were 1.25 kb, 1.5 kb and 3.8 kb, respectively. After agarose gel electrophoresis, the subgenomic RNA was immobilized on a nylon membrane filter (Pall Biodyne) and hybridized with $^{32}$P labeled clone DNA. Selected was a clone (pSPTNV127), which hybridized with the two 3' subgenomic TNV RNAs and contained a fragment located between positions 1900 and 2300 of the TNV RNA. Restriction analysis demonstrated that this fragment contained an internal HpaII fragment which could be used as a primer for the cDNA synthesis of the replicase gene which is located 5' terminally on the TNV RNA. For the preparatory cDNA cloning, however, use was made of a synthetic oligonucleotide, derived from the sequence of pSPTNV127: 5' GCTTGTGAGTATCA 3'. This sequence is complementary to the genomic RNA.

The synthesis of the cDNA was performed as described hereinabove but in the presence of methyl-mercury-hydroxide to make it easier for the RNA to be copied (Lenstra et al., Gen. Anal. Techn. 5, 57–61, 1988). Thus a 2.2 kb strand was obtained which corresponds to the region of the replicase gene of TNV. After cloning into pSP64, from 1500 clones three clones were selected which contain a 2.2 kb fragment in the sense orientation relative to the SP6 promoter.

Using SP6 polymerase and starting from the one pSPTNV94, RNA was prepared which, in a wheat germ extract, led inter alia to synthesis of a 73 kD protein, which is the expected molecular weight of the TNV replicase.

In this experiment $^{35}$S methionine was used during the protein synthesis and the 73 kD protein was detected after SDS PAGE and autoradiography.

The sequence of pSPTNV94 was determined by the dideoxy method of Sanger et al. (Proc. Natl. Acad. Sci. USA 74, 5463–5467, 1977) after cloning of fragments into pUC18 plasmid. The strategy for determining the nucleotide sequence is presented in FIG. 3 and the sequence in FIGS. 4a–4e.

The fragment in pSPTNV127 appeared to contain the 3' end of the replicase gene. To obtain a complete clone of the replicase gene of TNV, use was made of a unique XmaI site in pSPTNV94 and pSPTNV127 DNA and a unique SacI site in the polylinker of pSP64. By a ligation of the small XmaI-SacI fragment of pSPTNV127 in the large pSPTNV94 fragment with XmaI and SacI ends, pSPTNV rep-1 was obtained. The clone is 2236 bases long, the longest open reading frame being found from base 50 to base 2221 (absolute reading frame relative to the first base: 2) with an internal stop codon at position 656. This open reading frame, after translation and use of a suppressor tRNA at position 656–658, codes for a replicase of 724 amino acids. For further uses, the internal stop codon TAG, by means of specific mutagenesis, was changed into a codon TAT, coding for Tyr.

An E. coli strain MC1061 [PSPTNV rep-1], which contains the plasmid pSPTNV rep-1, was registered on Jul. 26, 1990 with the Centraal Bureau voor Schimmelculturen (CBS), Baarn, the Netherlands, under number CBS 336.90.

EXAMPLE IV

Expression, with amplification of the messenger RNA by TNV replicase, of a chloramphenicol-acetyl-transferase gene, fused with a part of the STNV coat protein gene 1. Construction of a DNA sequence in which a part of the STNV coat protein gene is fused with the chloramphenicol-acetyl-transferase gene The plasmid pSTNV N198 was described by Van Emmelo et al. (Virology 157, 480–487, 1987). It contains a 14 bp NcoI linker in the EcoRV site of the coat protein gene of STNV. By cutting with NcoI, filling in the ends with E. coli polymerase and back ligation the reading frame was recovered again: Asp(56)/Ser-Met-His-Gly-Asn-Ser/Ile(57).

The plasmid obtained gives rise to the formation of STNV infective particles in coinfections with TNV of Phaseolus leaves (Vigna unguiculata, cowpea). This plasmid was called pSTNV N202. The PstI fragment, containing the STNV cDNA N202, was transcloned into pSP65 (Promega). The plasmid obtained was called pSPSTNV N202 (FIG. 5). From pBR325 the chloramphenicol-acetyl-transferase gene (CAT gene) was taken as TaqI fragment, which was then blunt-ended with the Klenow fragment of E. coli DNA polymerase. pSPSTNV N202 was cut with NsiI and blunt-ended. Then the TaqI fragment was cloned into the NsiI deleted pSPSTNV N202 plasmid.

The sense orientation relative to the SP6 promoter was called pSPSTNV CAT-1 and the non-sense orientation PSP-STNV CAT-2 (see FIG. 5).

2. Expression of the chimeric CAT gene using TNV virus in Phaseolus (Vigna unguiculata) leaves Leaves of cowpea were infected with either TNV and STNV plasmid, or TNV and pSPSTNV CAT-1. Forty hours after inoculation the leaves were extracted with PBS buffer with 0.1% Triton X100 and the extract was treated with anti-STNV coat protein serum. Immunoprecipitation with protein A-sepharose was followed by frequent washing.

The chloramphenicol-acetyl-transpherase activity was determined on the complexes with 1-$^{14}$C-acetyl-coenzyme A and chloramphenicol as described by Gorman et al. (Molec. Cell. Biol. 2, 1044–1081, 1982) and by De Block et al. (EMBO J. 3, 1681–1689, 1984).

CAT activity could only be demonstrated in the leaves which were infected with TNV and pSPSTNV CAT-1 and the extract of which was treated with STNV antiserum (the results are not shown here).

3. Multiplication of the STNV-CAT RNA

Two days after inoculation of cowpea leaves with TNV and pSPSTNV CAT-1 DNA, the leaves were harvested and the nucleic acid fraction was isolated. DNA was removed with RNAase-free DNAase I and the RNA was analyzed by Northern hybridization with CAT specific, $^{32}$P labeled DNA (TaqI fragment from pBR325) Both in the ss RNA and the ds RNA fraction a band of about 1750 nucleotides was detected (the results are not shown here). This clearly demonstrates that the pSPSTNV CAT-1 plasmid DNA is converted by TNV into ss and ds STNV CAT-1 RNA.

DESCRIPTION OF THE FIGURES

FIG. 2 shows the map of the plasmid pMP90RK. At the location where the KpnI fragments 9 and 12 of pGV 3100 adjoin one another, the T-DNA including of the border sequences was deleted. The virulence region is entirely intact. By exchange recombination the gene for gentamycin resistance (Gm) and a fragment of pRK 2013, which carries the genes for transfer (tra1, tra2 and tra3), replication (trfa) and kanamycin resistance (Km), were inserted.

Figure 1:
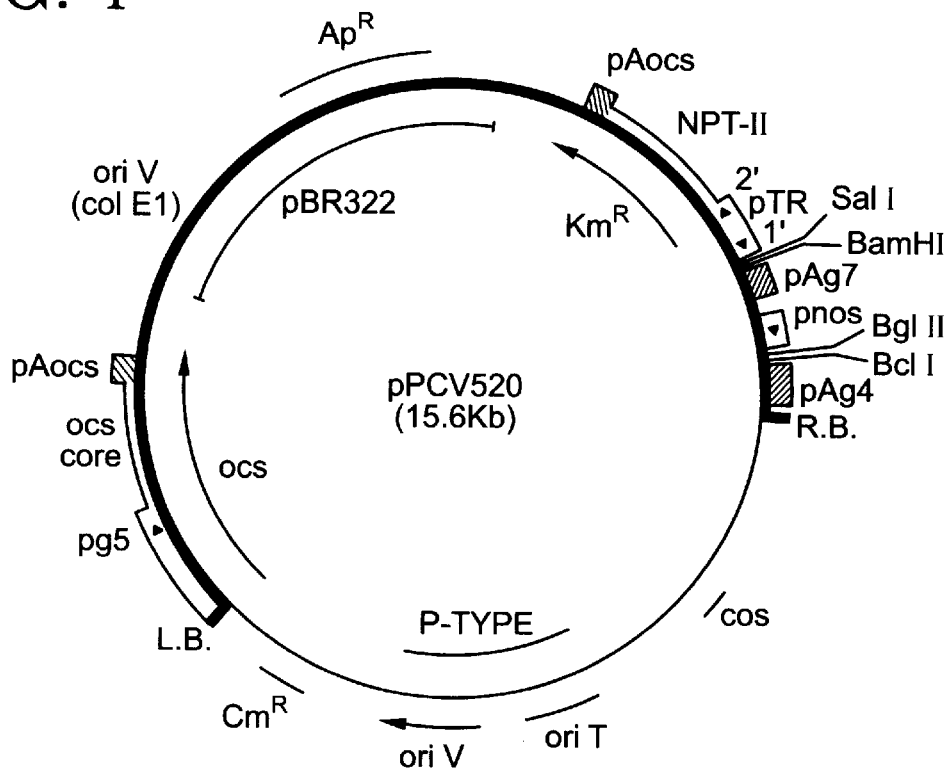
FIG. 1 shows the map of the plasmid pPCV 520. The T-DNA of this plasmid is indicated by a thick line and is bounded by left-hand (LB) and right-hand (RB) border sequences; the unique restriction sites for SalI and BamHI can be used for cloning fragments between the plant promoter pTR1' and the polyadenylation signal pAg7, and the restriction sites BglII and BclI for cloning between pnos and pAg4. The kanamycin resistance gene NPT-II is expressed by pTR2' and pAocs. The octopine gene is expressed with the tissue-specific promoter pg5 and pAocs. The pBR322-sequences with the replication-origin (oriV, colE1) and the ampicillin resistance (Ap) are located in the T-DNA. The pRK2 origin of replication (ori V) and transfer (ori T), the chloramphenicol resistance gene (Cm) and the cohesive ends of lambda (cos) are located outside the T-DNA.
Figure 2:
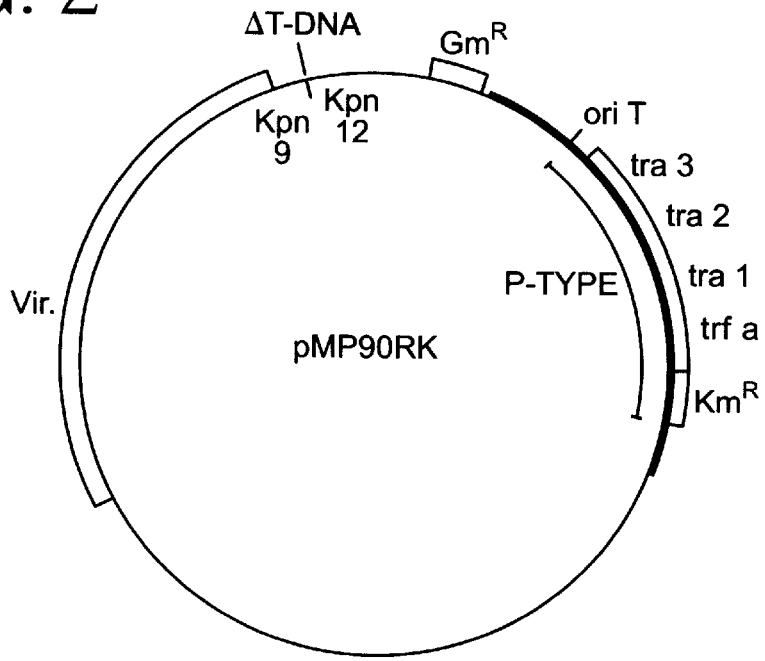
Figure 3:
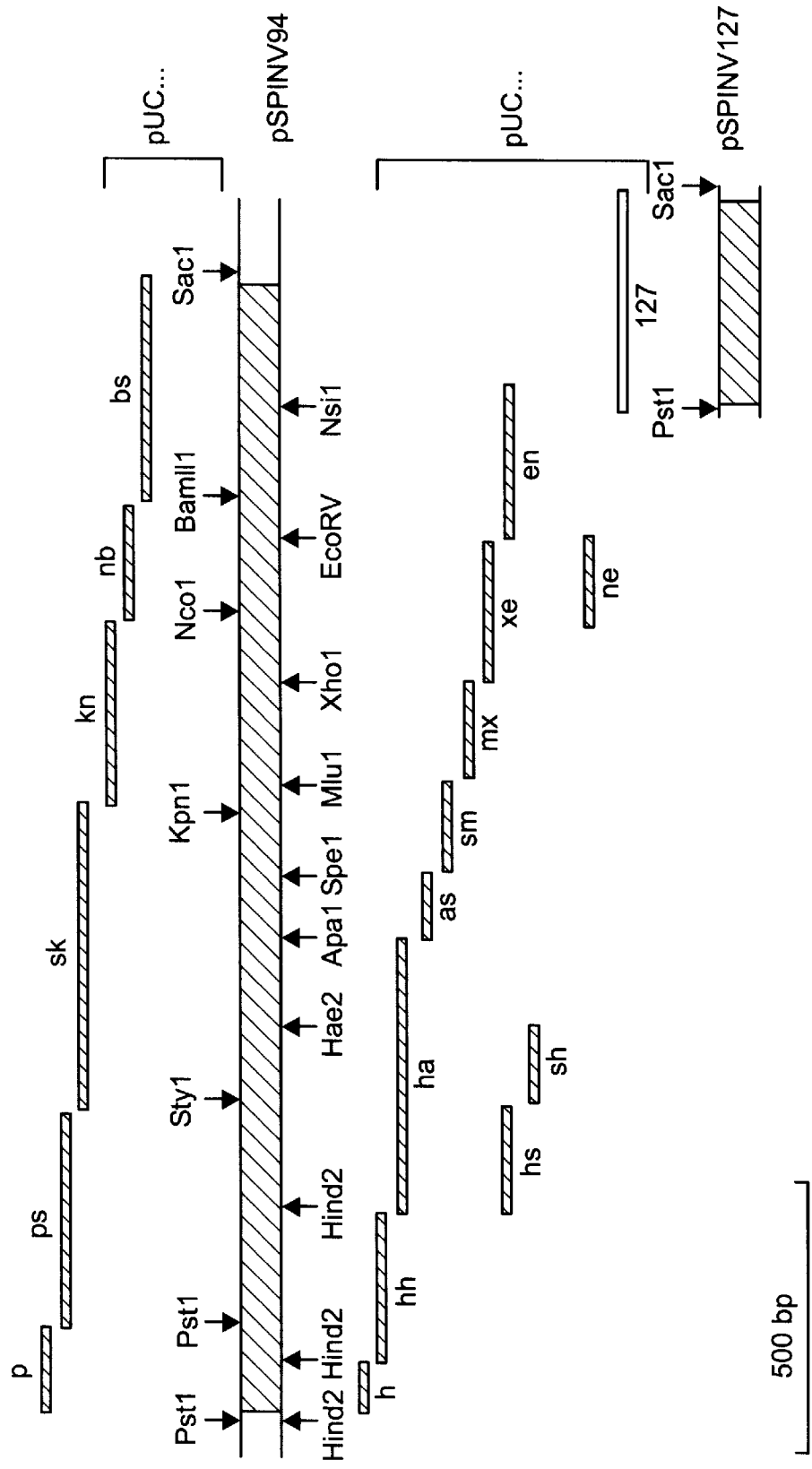

FIG. 3 schematically shows the restriction map of the region of the TNV replicase gene and the fragments used for determining the sequence. After cloning into pUC18 the fragments were analyzed in both directions or twice according to the dideoxy method of Sanger to determine the nucleotide sequence.

FIGS. 4*a*–4*e* show the complete sequence of the replicase gene of TNV. The amino acid sequence exhibits homology with the replicase genes of CarMV (Carnation Mottle Virus) and TuCV (Turnip Crinkle Virus) . The amber stop codon at position 656 is present in the natural genome. For further uses this stop codon was replaced by TAT which codes for the amino acid Tyr. The initiation and stop codons are indicated by ▲ and ▼, respectively. The amino acid sequence starts at nucleotide position 50 and stops at position 2221.

Figure 5:
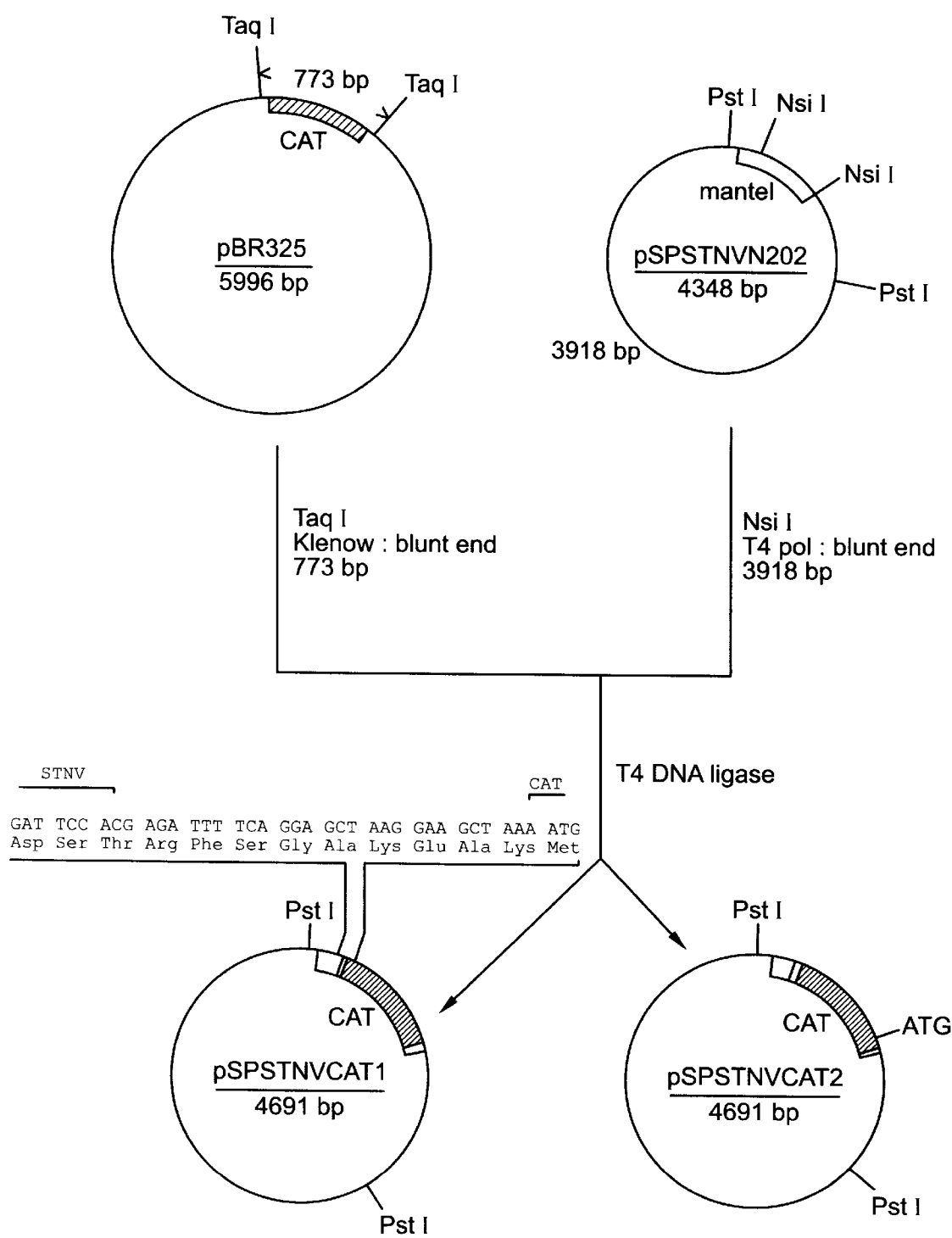

FIG. 5 schematically shows the construction of the plasmids pSPSTNVCAT1 and pSPSTNVCAT2. Details about this construction are described in Example IV.

TABLE 1

| STNV mutant | *E. coli* NF1 coat protein | cowpea coat protein | ssRNA | dsRNA |
|---|---|---|---|---|
| wild type | + | + | ++ | ++ |
| N162 | + (short) | – | + | ++ |
| N164 | + (+6 a.a.) | + (+6 a.a.) | ++ | ++ |
| S164 | + (short) | – | + | ++ |
| Brad | + (+10 a.a.) | + (+10 a.a.) | ++ | ++ |
| N198 | + (short) | – | + | ++ |
| N200 | + (+6 a.a.) | + (+6 a.a.) | ++ | ++ |
| S200 | + (+12 a.a.) | – | + | ++ |
| N320 | + (short) | – | + | ++ |
| N322 | + (+6 a.a.) | – | + | ++ |
| N531 | + (short) | – | + | ++ |

TABLE 1-continued

| STNV mutant | *E. coli* NF1 coat protein | cowpea coat protein | ssRNA | dsRNA |
|---|---|---|---|---|
| N533 | + (+6 a.a.) | – | + | ++ |
| S613 | + (+6 a.a.) | – | + | ++ |
| N843 | + | – | – | – |
| N164N843 | + (+6 a.a.) | – | – | – |

"a.a." stands for amino acids; "short" indicates a shortened coat protein. The presence and the size of the coat protein were determined by Western blotting. RNA was hybridized with an STNV-DNA probe, which was labeled with $^{32}P$.

TABLE 2

| STNV and control | STNV coat protein | | STNV RNA (ds and ss) with STNV DNA | | | | |
|---|---|---|---|---|---|---|---|
| plants | – TNV | + TNV | – TNV | + TNV | 14 | 18 | 30 |
| N164.1 | – | + to +++ | – | + to +++ | – | + | – |
| N164.2 | – | + to +++ | – | + to +++ | – | + | – |
| N164N843.1 | – | ++ to +++ | – | ++ to +++ | + | + | – |
| N164N843.2 | – | + to +++ | – | + to +++ | + | + | – |
| Brad.1 | – | + to +++ | – | + to +++ | – | – | + |
| Brad.2 | – | ++ | – | ++ | – | – | + |
| tobacco SR1 | – | – | – | – | | | |
| 520 | – | – | – | – | | | |

Of the transformed plants, per STNV mutant several independently isolated plants were tested. STNV coat protein (+6 and +10 amino acids) was determined by Western blotting, RNA by Northern hybridization with $^{32}P$-labeled STNV-DNA. Independent transformants with the same mutant genome yielded signals of different intensity, which is indicated by the number of + signs. For the Western and Northern blottings per sample 10 mg leaf material was used. By hybridization with the various linkers (14-, 18- and 30-mer) the identity of the STNV genomes was confirmed.

We claim:

1. A method of protecting plants or plant cells against an RNA-based plant virus which for its replication is dependent upon a viral RNA/RNA polymerase, comprising:

a) obtaining a plant RNA defective replicon which is a stripped viral replicon of said RNA-based plant virus, wherein said stripped viral replicon comprises cis elements for replication but is devoid of genes coding for viral RNA/RNA polymerase and viral coat protein and wherein said stripped viral replicon is not able to replicate independently, but replicates more efficiently in the presence of the viral RNA/RNA polymerase than the RNA of the wild-type plant virus, b) preparing an expression cassette functional in plants or plant cells, said expression cassette comprising said stripped viral replicon between two inverted repeat nucleotide sequences of 12–250 bp, and c) incorporating said expression cassette into the genome of said plants or plant cells to be protected.

2. A method according to claim 1, wherein said stripped viral replicon also comprises cis elements for transport.

3. A method according to claim 1, wherein said stripped viral replicon also comprises cis elements for packing in coat protein.

4. A method according to claim 1, wherein said stripped viral replicon also comprises cis elements for translation.

5. A method according to claim 1, wherein said stripped viral replicon is obtained by isolating viral RNA from particles of said RNA-based plant virus or from infected plants or plant cells, infecting plants or plant cells with the isolated viral RNA, such that the viral RNA is replicated, isolating replicated viral RNA from infected plants or plant cells and repeating said steps of infecting plants or plant cells with isolated viral RNA and isolating replicated viral RNA from infected plants or plant cells until the replicated viral RNA includes viral RNA species which represent a stripped viral replicon comprising cis elements for replication but being devoid of genes coding for viral RNA/RNA polymerase and viral coat protein, wherein said stripped viral replicon is not able to replicate independently but replicates more efficiently in the presence of the viral RNA/RNA polymerase than the RNA of the wild-type plant virus.

6. A method according to claim 1, wherein said RNA-based plant virus is a positive strand virus.

7. A method according to claim 6, wherein said positive strand virus is Tobacco Necrosis Virus.

8. A method of protecting tobacco plants or plant cells against an RNA-based tobacco plant virus which for its replication is dependent upon a viral RNA/RNA polymerase, comprising:

a) obtaining a plant RNA defective replicon which is a stripped viral replicon of said RNA-based tobacco plant virus, wherein said stripped viral replicon comprises cis elements for replication but is devoid of genes coding for viral RNA/RNA polymerase and viral coat protein and wherein said stripped viral replicon is not able to replicate independently, but replicates more efficiently in the presence of the viral RNA/RNA polymerase than the RNA of the wild-type plant virus, b) preparing an expression cassette functional in tobacco plants or plant cells, said expression cassette comprising said stripped viral replicon between two inverted repeat nucleotide sequences of 12–250 bp, and c) incorporating said expression cassette into the genome of said tobacco plants or plant cells to be protected.

9. A method according to claim 8, wherein said stripped viral replicon also comprises cis elements for transport.

10. A method according to claim 8, wherein said stripped viral replicon also comprises cis elements for packing in coat protein.

11. A method according to claim 8, wherein said stripped viral replicon also comprises cis elements for translation.

12. A method according to claim 8, wherein said stripped viral replicon is obtained by isolating viral RNA from particles of said RNA-based tobacco plant virus or from infected tobacco plants or plant cells, infecting tobacco plants or plant cells with the isolated viral RNA, such that the viral RNA is replicated, isolating replicated viral RNA from infected tobacco plants or plant cells and repeating said steps of infecting tobacco plants or plant cells with isolated viral RNA and isolating replicated viral RNA from infected tobacco plants or plant cells until the replicated viral RNA includes a viral RNA species which represents a stripped viral replicon comprising cis elements for replication, but which are devoid of genes coding for viral RNA/RNA polymerase and viral coat protein, wherein said stripped viral replicon is not able to replicate independently, but replicates more efficiently in the presence of the viral RNA/RNA polymerase than the RNA of the wild-type plant virus.

13. A method according to claim 8, wherein said RNA-based tobacco plant virus is a positive strand virus.

14. A method according to claim 13, wherein said positive strand virus is Tobacco Necrosis Virus.

\* \* \* \* \*

UNITED STATES PATENT AND TRADEMARK OFFICE
CERTIFICATE OF CORRECTION

PATENT NO.   : 6,197,542 B1
DATED        : March 6, 2001
INVENTOR(S)  : Van Haute et al.

It is certified that error appears in the above-identified patent and that said Letters Patent is hereby corrected as shown below:

Column 17,
Line 17, now reads "Accordingly the in vitro constructed" should read -- For comparison the in vitro constructed --;

Column 10,
Line 5, now reads "N200 the mutants pBR STNV S164 and 5200" should read -- N200 the mutants pBR STNV S164 and S200 --.

Signed and Sealed this

Eighth Day of January, 2002

*Attest:*

*Attesting Officer*

JAMES E. ROGAN
*Director of the United States Patent and Trademark Office*